(12) United States Patent
Schaller et al.

(10) Patent No.: US 9,693,814 B2
(45) Date of Patent: Jul. 4, 2017

(54) TORQUE LIMITING INSTRUMENT, SYSTEM AND RELATED METHODS

(71) Applicant: DePuy Synthes Products, Inc., Raynham, MA (US)

(72) Inventors: Konrad Schaller, Oberdorf (CH); Cyril Voisard, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 936 days.

(21) Appl. No.: 13/826,718

(22) Filed: Mar. 14, 2013

(65) Prior Publication Data

US 2014/0276893 A1 Sep. 18, 2014

(51) Int. Cl.
*A61B 17/88* (2006.01)
*B25G 3/02* (2006.01)
*B25B 23/00* (2006.01)
*B25B 23/142* (2006.01)
*A61B 90/00* (2016.01)

(52) U.S. Cl.
CPC ...... *A61B 17/8875* (2013.01); *B25B 23/0042* (2013.01); *B25B 23/1427* (2013.01); *B25G 3/02* (2013.01); *A61B 2090/031* (2016.02); *Y10T 29/49826* (2015.01)

(58) Field of Classification Search
CPC ............ A61B 17/8875; B25B 23/1405; B25B 23/141; B25B 23/142; B25B 23/1422; B25B 23/1427
USPC ...................................... 81/467; 606/99, 104
See application file for complete search history.

(56) References Cited

U.S. PATENT DOCUMENTS

| 3,157,258 | A | 11/1964 | Cronholm et al. |
| 3,742,787 | A * | 7/1973 | Whiteford ............ B25B 13/465 81/438 |
| 5,337,638 | A | 8/1994 | Coss et al. |
| 5,507,211 | A | 4/1996 | Wagner |
| 5,615,587 | A | 4/1997 | Foerster, Jr. |
| 5,653,151 | A | 8/1997 | Blacklock |
| 5,746,298 | A | 5/1998 | Krivec et al. |
| 6,237,448 | B1 | 5/2001 | Haxton |
| 6,439,086 | B1 | 8/2002 | Bahr |
| 6,662,693 | B2 | 12/2003 | Hu |
| 6,666,112 | B2 | 12/2003 | Hu |
| 6,698,315 | B1 | 3/2004 | Wright |
| 6,698,316 | B1 | 3/2004 | Wright |
| 6,725,746 | B1 | 4/2004 | Wright |
| 6,880,433 | B1 | 4/2005 | Tanimura |
| 6,904,833 | B2 | 6/2005 | Wright |

(Continued)

*Primary Examiner* — Anu Ramana
(74) *Attorney, Agent, or Firm* — Baker & Hostetler LLP

(57) ABSTRACT

An instrument for limiting torque can include a method for limiting torque that is transferred from a handle of the instrument through a torque transfer member to a shaft that extends relative to the handle. The method can include applying a torque to the handle along a direction relative to the shaft. The method can include transmitting the applied torque from the handle through the torque transfer member to the shaft when the applied torque is less than a limited torque value. When the applied torque is greater than the limited torque value, at least one of the torque transfer member and the handle deforms so as to allow the handle to rotate along the direction relative to both the torque transfer member and the shaft.

19 Claims, 21 Drawing Sheets

(56) References Cited

U.S. PATENT DOCUMENTS

| | | |
|---|---|---|
| 7,127,955 B2 * | 10/2006 | Bondhus ............. B25B 23/1427 |
| | | 73/862.23 |
| 7,152,508 B2 | 12/2006 | McCalley, Jr. et al. |
| 7,159,494 B2 | 1/2007 | Jamnia et al. |
| 7,163,539 B2 | 1/2007 | Abdelgany et al. |
| 7,174,811 B2 | 2/2007 | Wright |
| 7,188,556 B1 | 3/2007 | Rinner |
| 7,243,580 B2 | 7/2007 | Frazee |
| 7,243,581 B1 | 7/2007 | Gao |
| 7,313,990 B1 | 1/2008 | Shiao |
| 7,318,776 B2 | 1/2008 | Honda |
| 7,383,756 B1 | 6/2008 | Liu |
| 7,451,674 B2 | 11/2008 | Edgar |
| 7,455,123 B2 | 11/2008 | Aeberhard |
| 7,467,576 B2 | 12/2008 | Gao |
| 7,487,700 B2 | 2/2009 | Cutler et al. |
| 7,506,694 B2 | 3/2009 | Stirm et al. |
| 7,597,032 B2 | 10/2009 | Baumgartner |
| 7,762,164 B2 | 7/2010 | Nino et al. |
| 7,810,416 B2 | 10/2010 | Cutler et al. |
| 7,926,391 B2 | 4/2011 | Hu |
| 7,938,046 B2 | 5/2011 | Nino et al. |
| 7,967,683 B2 | 6/2011 | Chuang |
| 7,987,930 B2 | 8/2011 | Purcell |
| 8,051,757 B2 | 11/2011 | Maddalon |
| 8,113,095 B2 | 2/2012 | Gao |
| 8,136,431 B2 | 3/2012 | Wengreen |
| 8,172,003 B2 | 5/2012 | Robieu et al. |
| 8,220,369 B2 | 7/2012 | Lai |
| 8,221,431 B2 | 7/2012 | Chenaux |
| 8,235,137 B2 | 8/2012 | Walker et al. |
| 8,317,791 B2 | 11/2012 | Phan |
| 8,443,702 B2 | 5/2013 | Kan et al. |
| 8,490,649 B2 | 7/2013 | Dolenti et al. |
| 8,495,935 B2 | 7/2013 | Mountz et al. |
| 8,549,963 B2 | 10/2013 | Chuang |
| 8,602,899 B2 | 12/2013 | You |
| 8,845,521 B2 * | 9/2014 | Maruyama ........... A61B 1/0057 |
| | | 464/37 |
| 9,504,528 B2 * | 11/2016 | Ivinson ................ B25B 23/141 |
| 2001/0004610 A1 | 6/2001 | Casutt |
| 2005/0148905 A1 | 7/2005 | Frazee |
| 2007/0137441 A1 | 6/2007 | Wright |
| 2009/0192501 A1 * | 7/2009 | Miletto .............. A61B 17/8875 |
| | | 606/1 |
| 2010/0107829 A1 | 5/2010 | Zimmerman et al. |
| 2010/0257979 A1 | 10/2010 | Zhan |
| 2010/0275746 A1 | 11/2010 | Wengreen |
| 2011/0042176 A1 | 2/2011 | Witte |
| 2011/0088520 A1 | 4/2011 | Albrecht |
| 2012/0130388 A1 | 5/2012 | Plotkin |
| 2012/0198972 A1 | 8/2012 | Nino et al. |
| 2012/0291599 A1 | 11/2012 | Cutler |
| 2012/0319190 A1 | 12/2012 | Zhu et al. |
| 2012/0325509 A1 | 12/2012 | Puzio et al. |
| 2013/0152746 A1 | 6/2013 | Kerboul et al. |
| 2013/0199345 A1 | 8/2013 | Nino et al. |
| 2013/0205569 A1 | 8/2013 | Nino et al. |

* cited by examiner

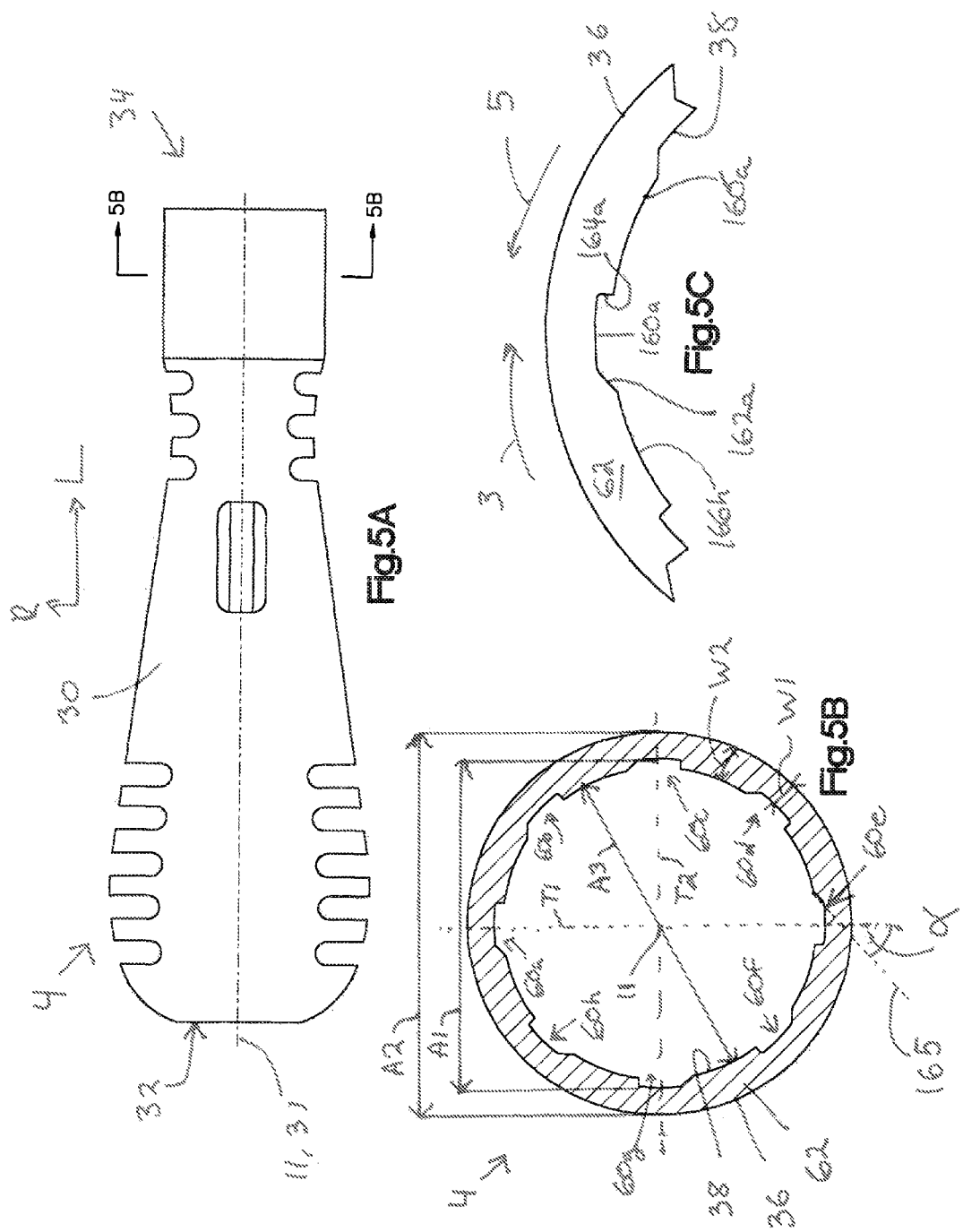

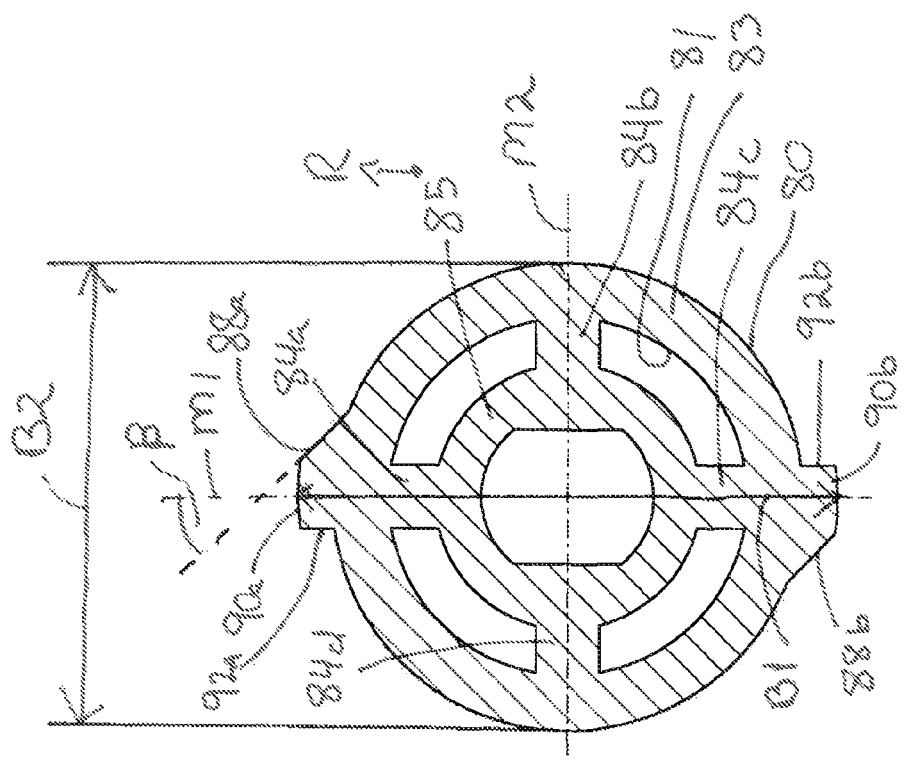
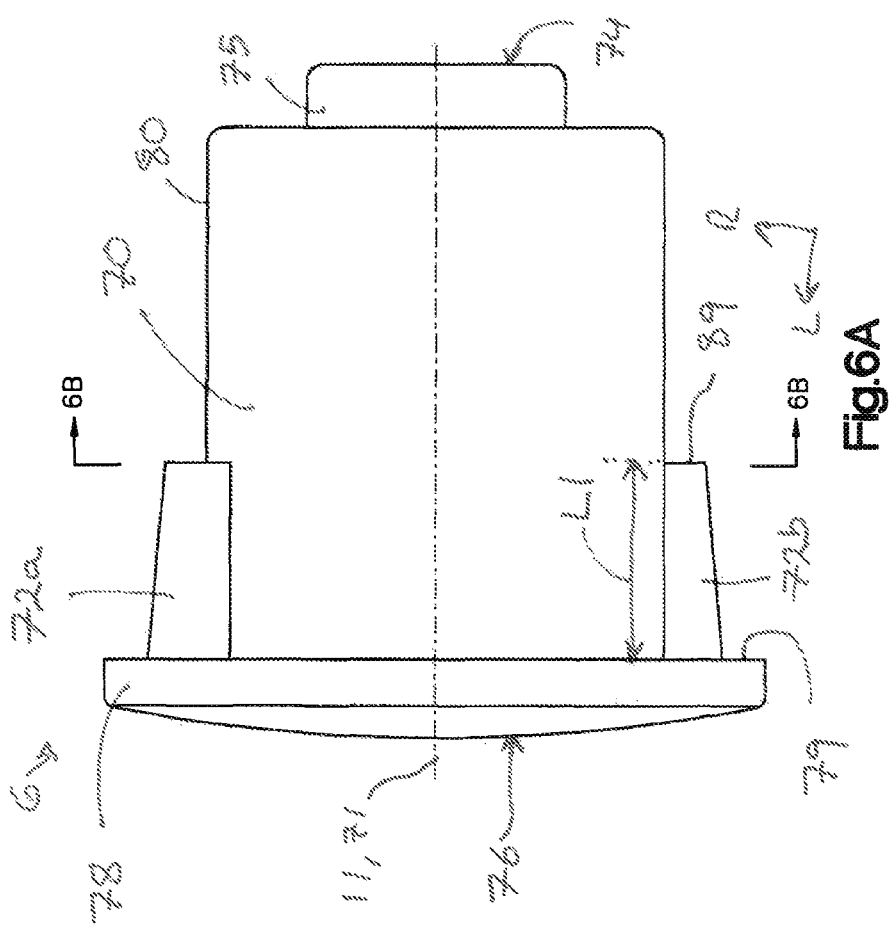
Fig.6A
Fig.6B

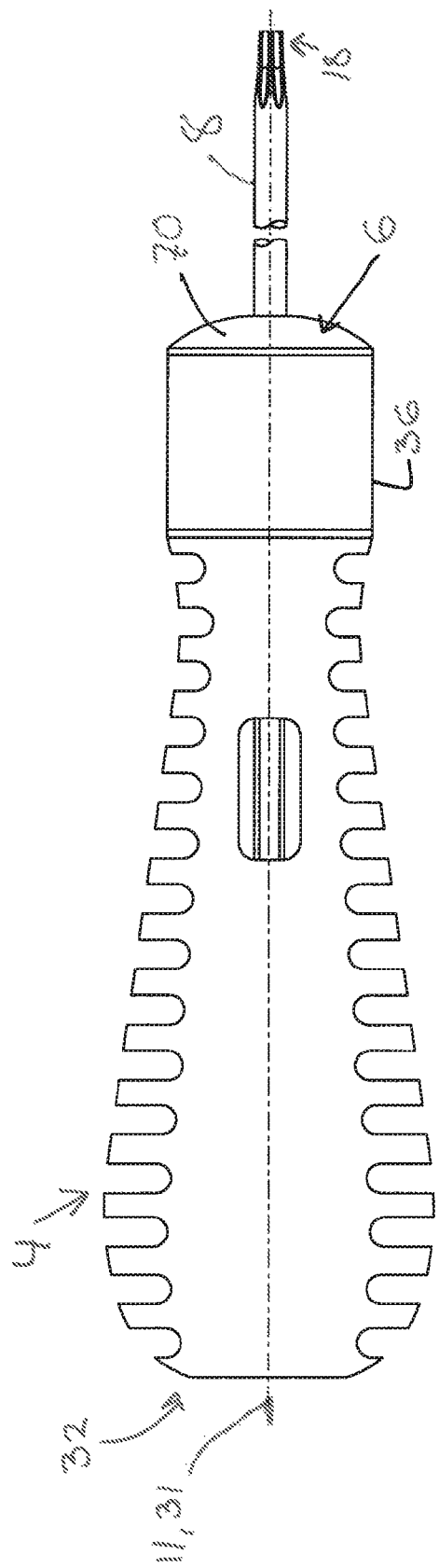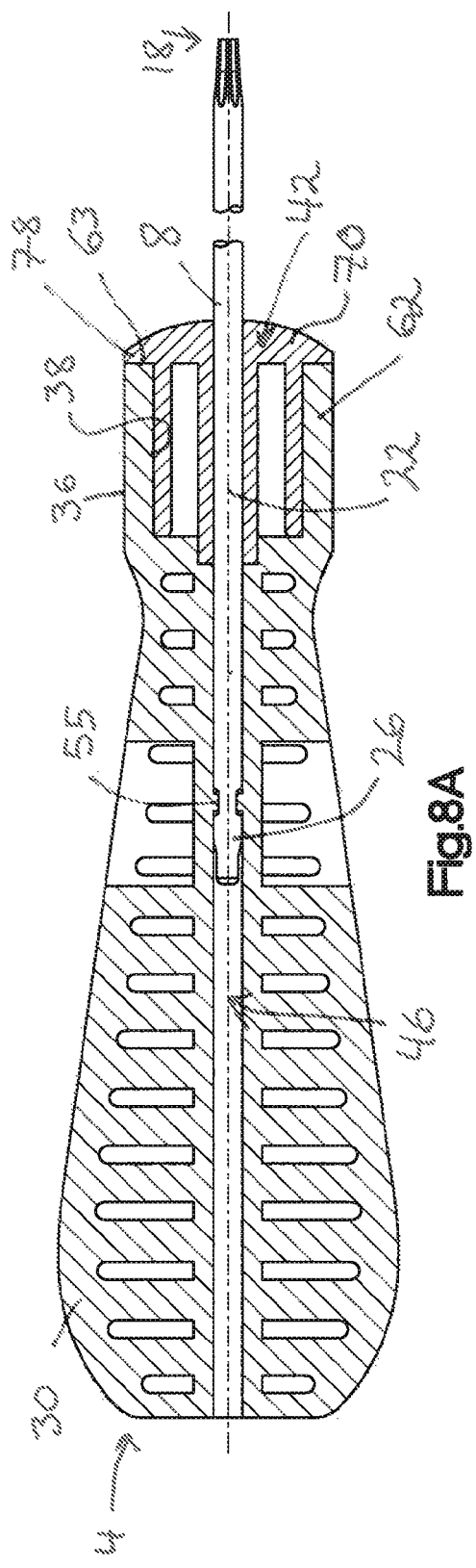
Fig.7
Fig.8A

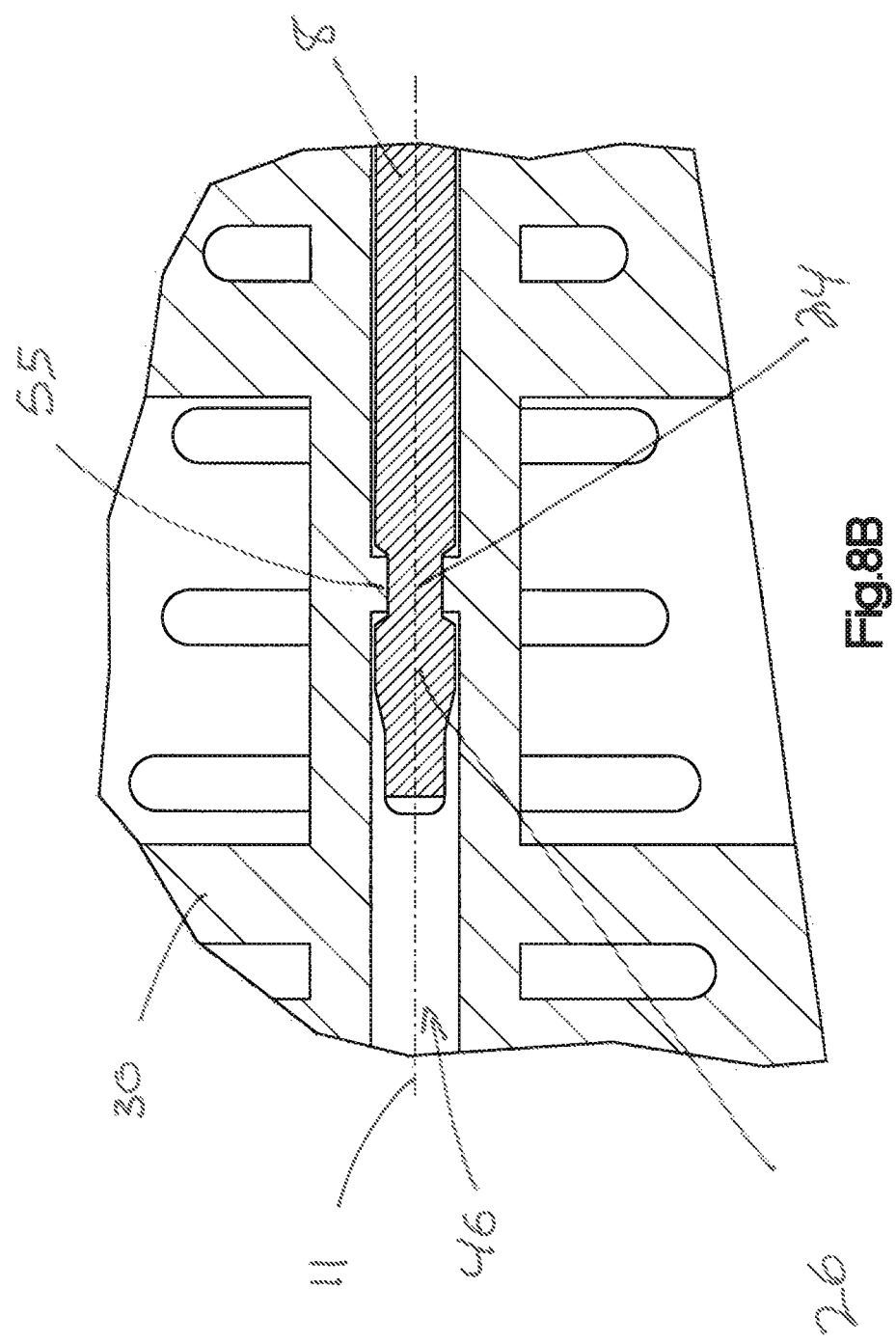

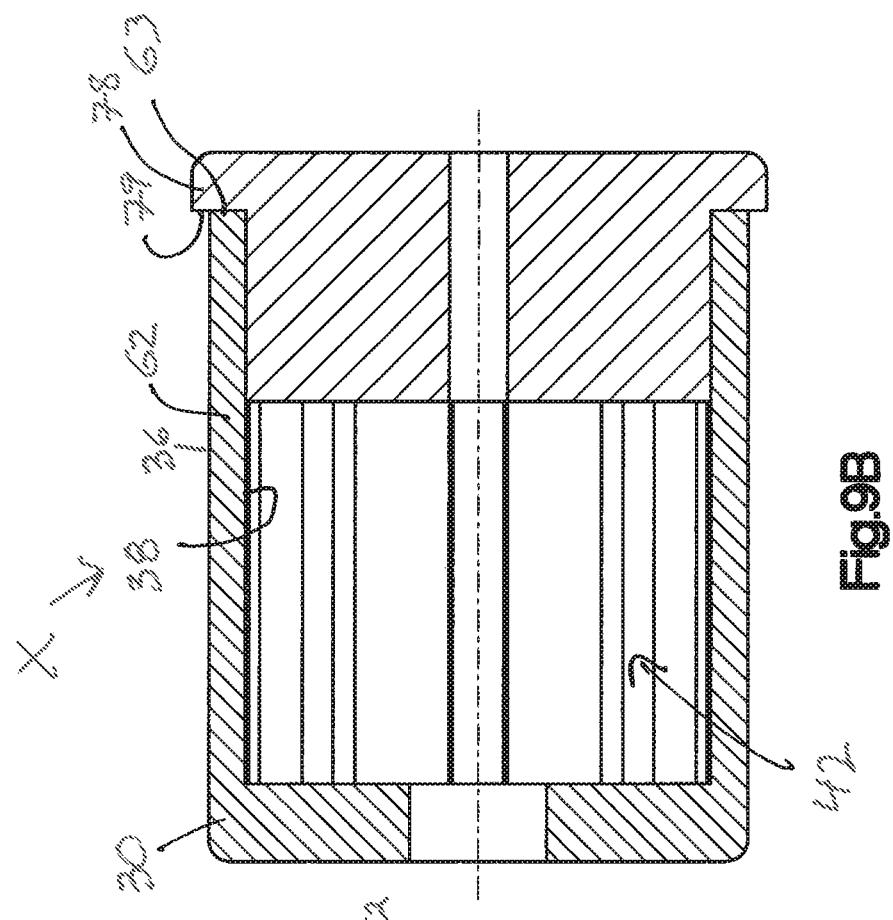
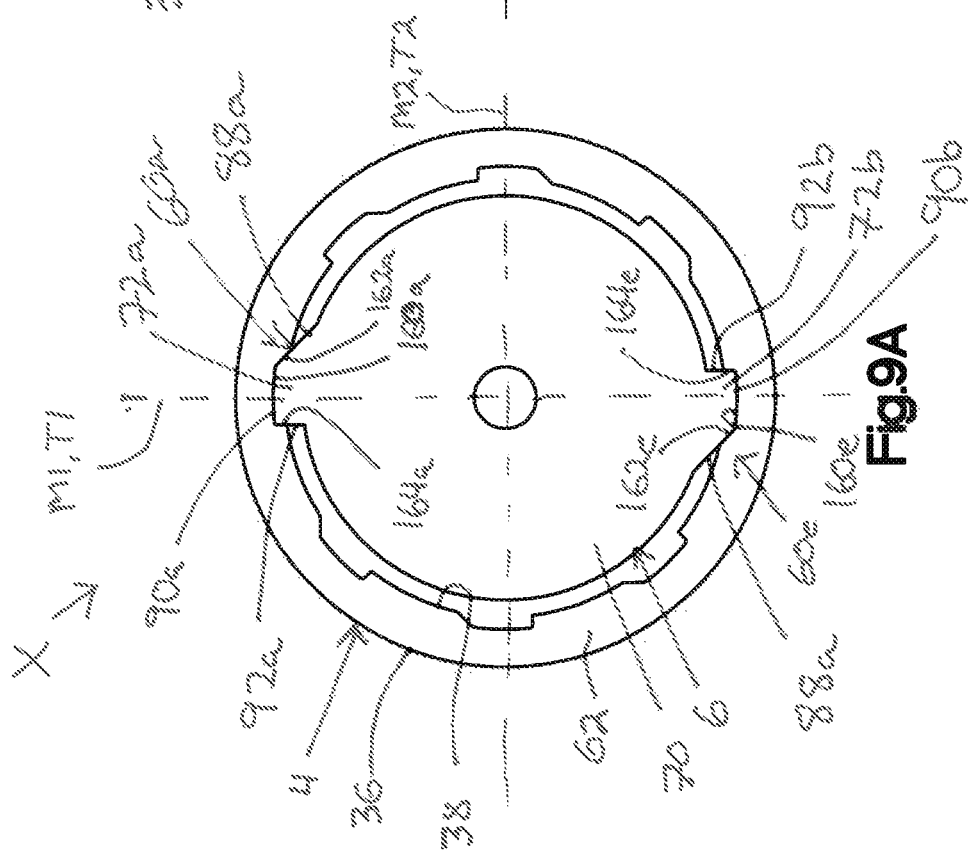

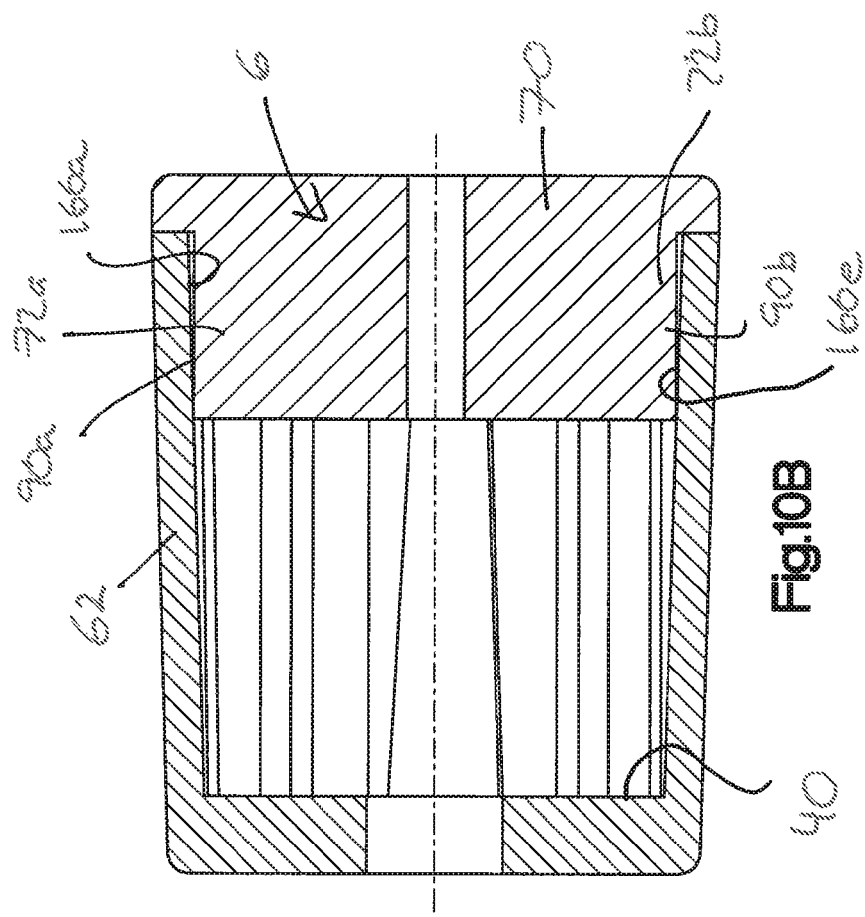
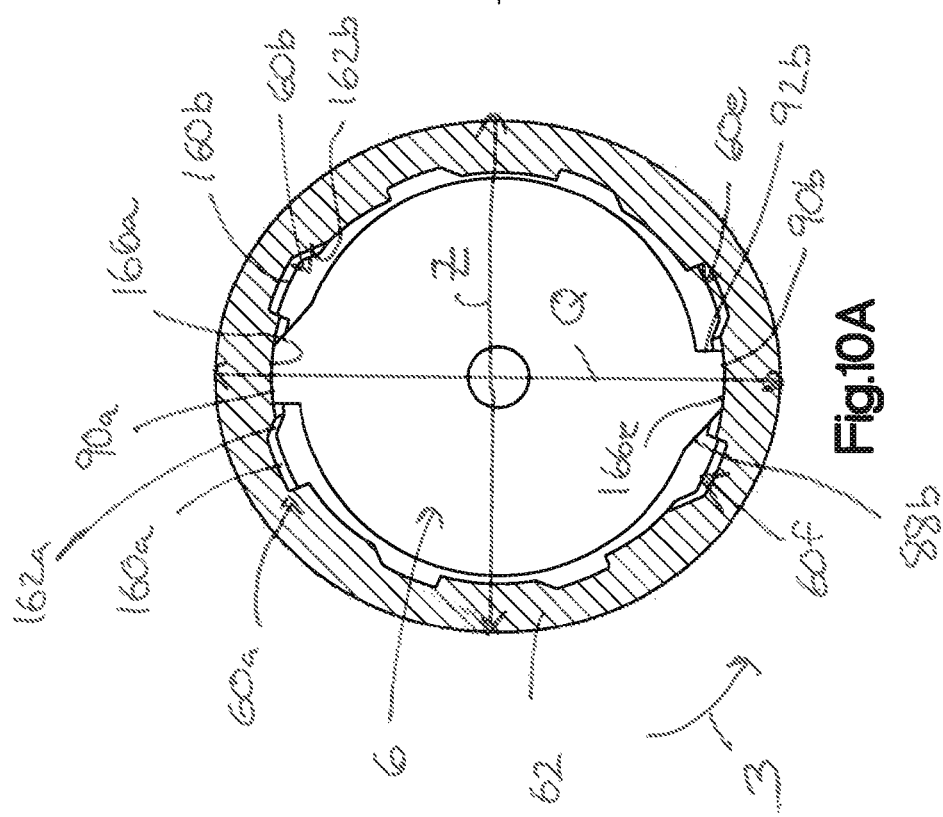

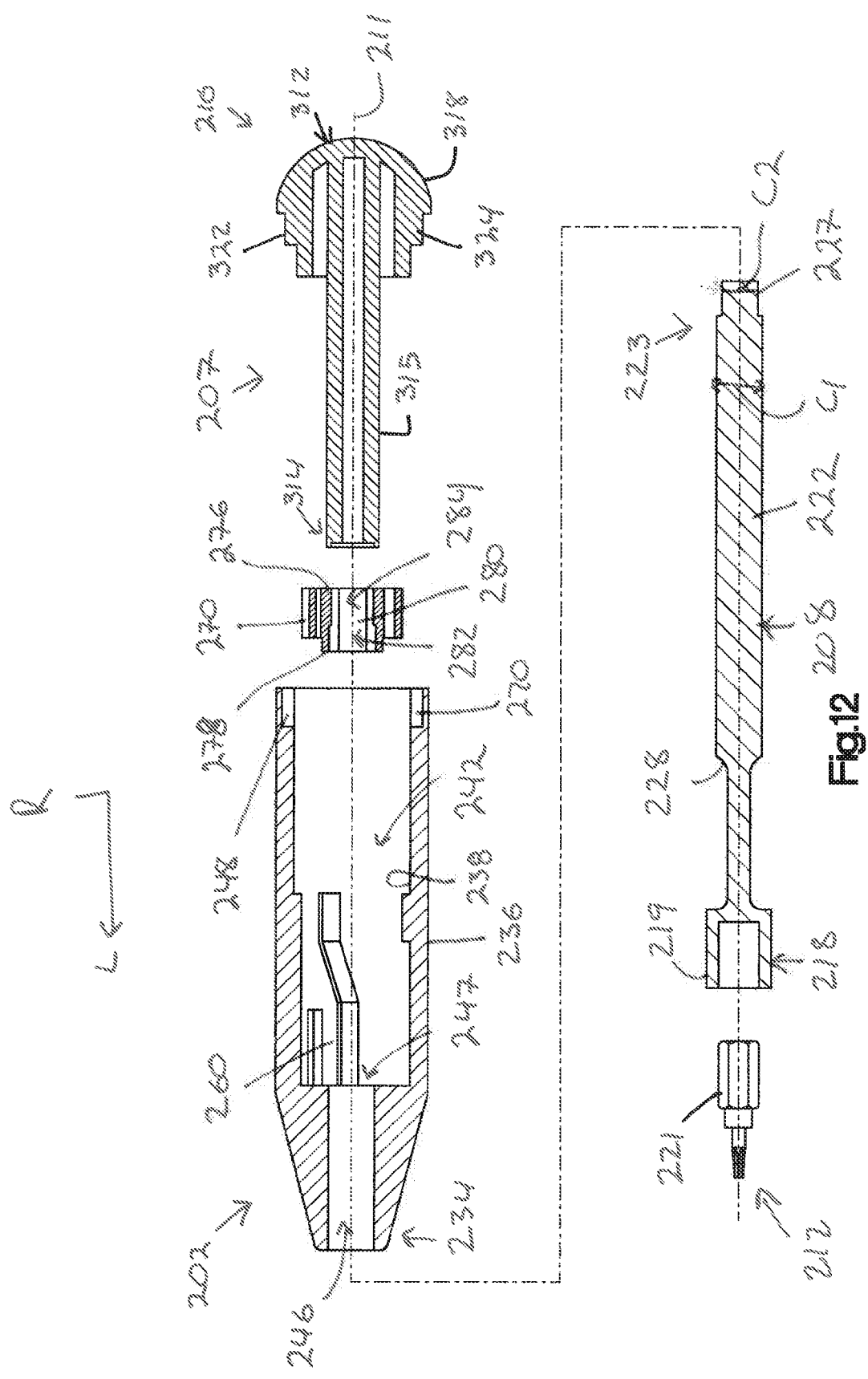

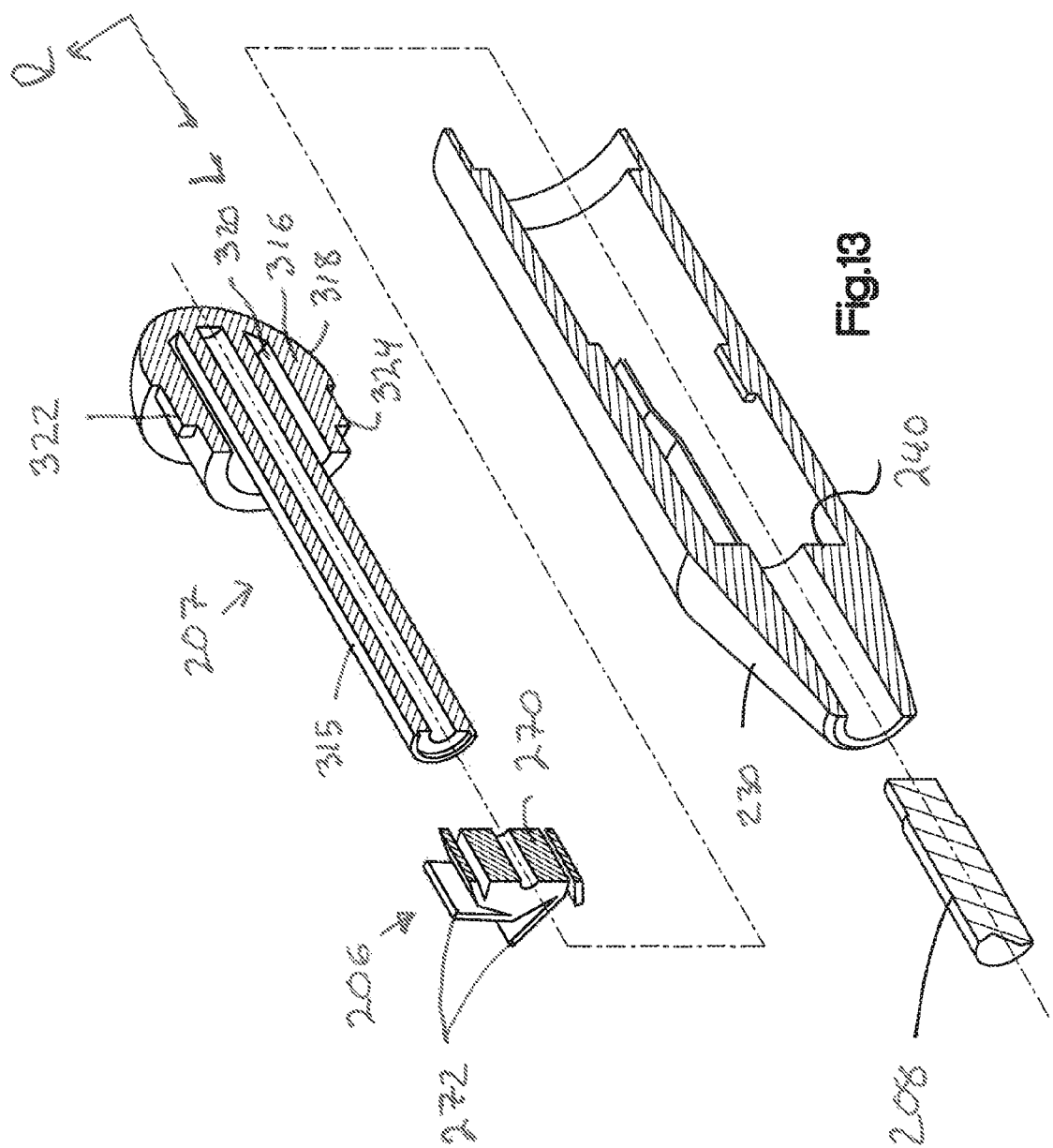

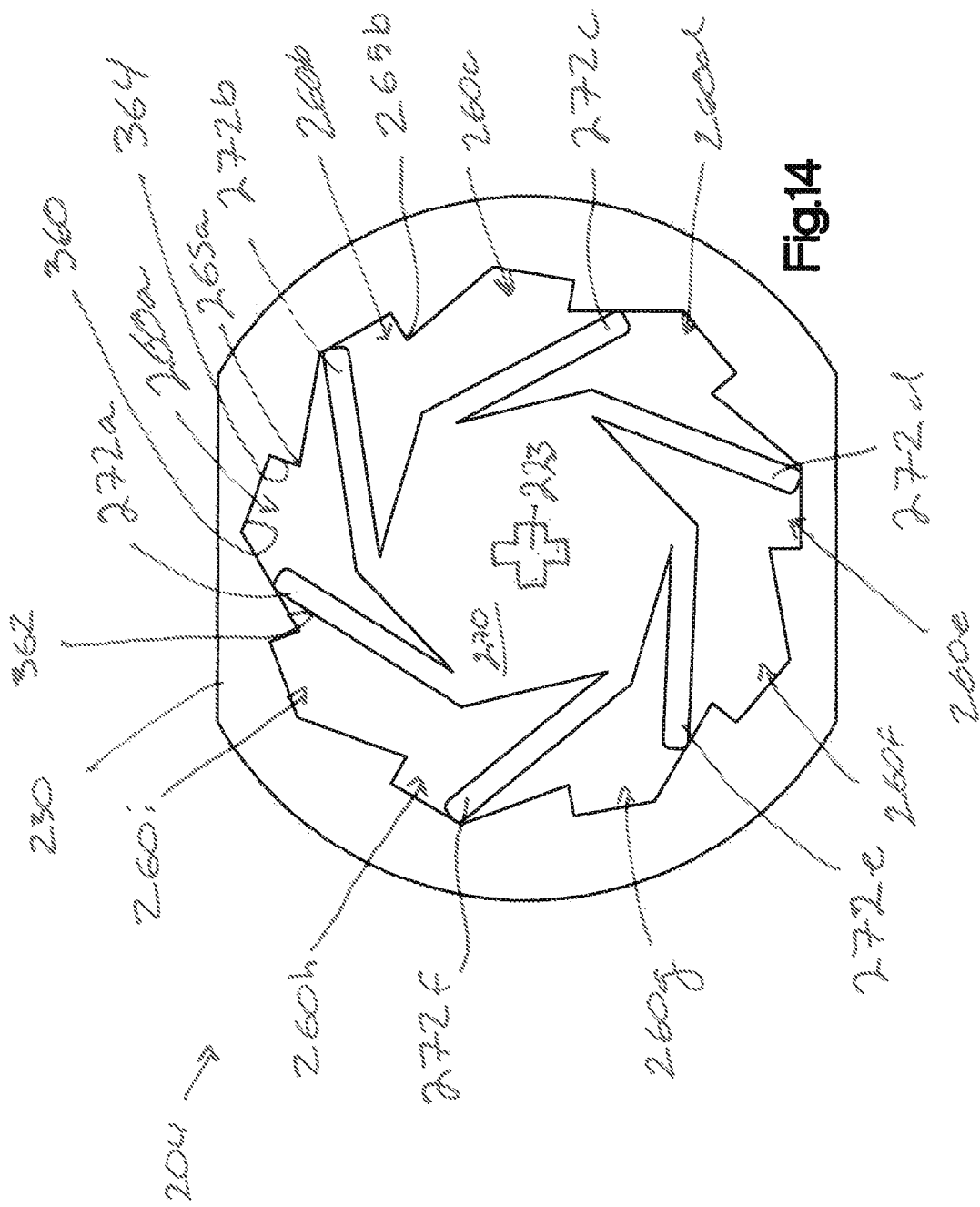

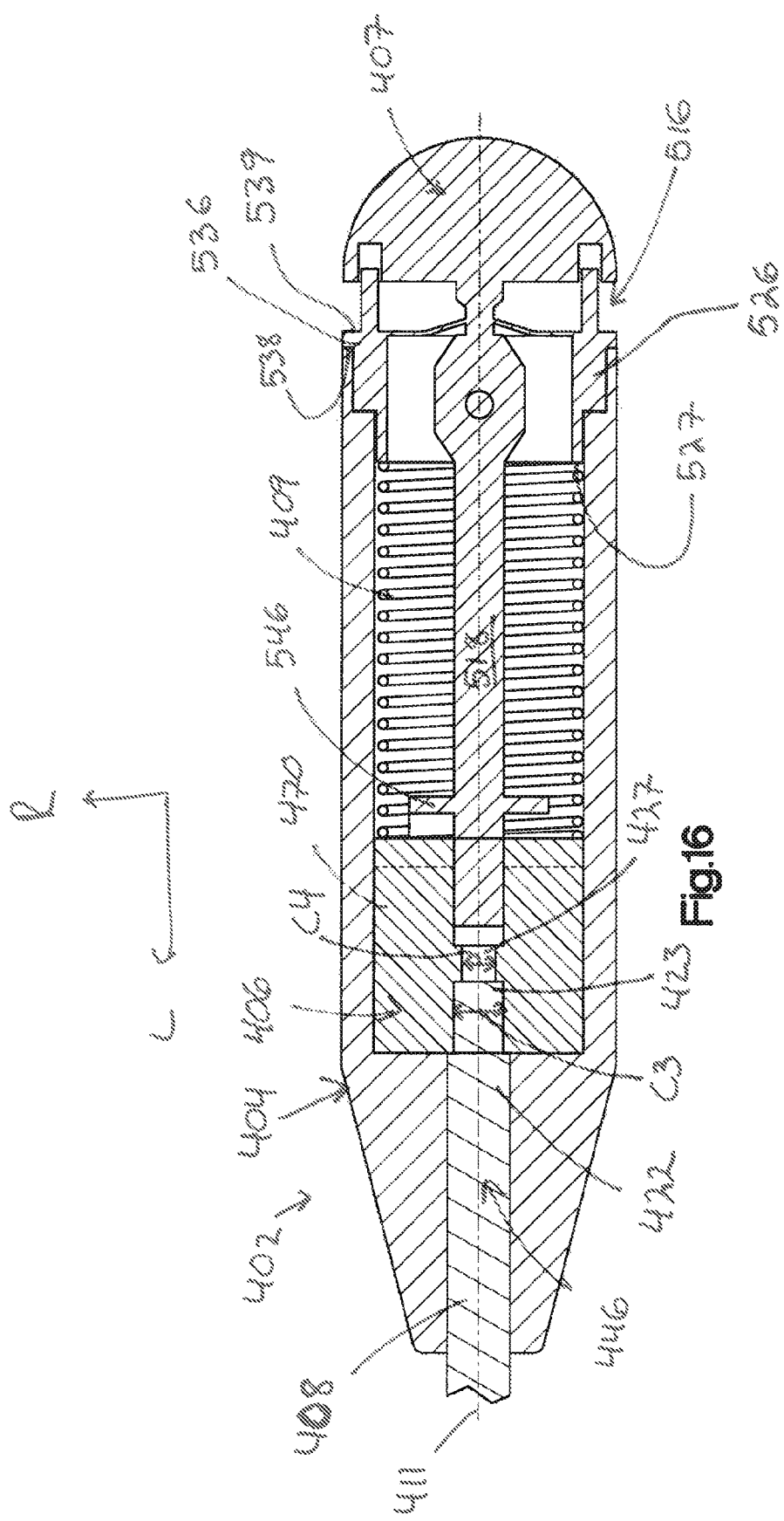

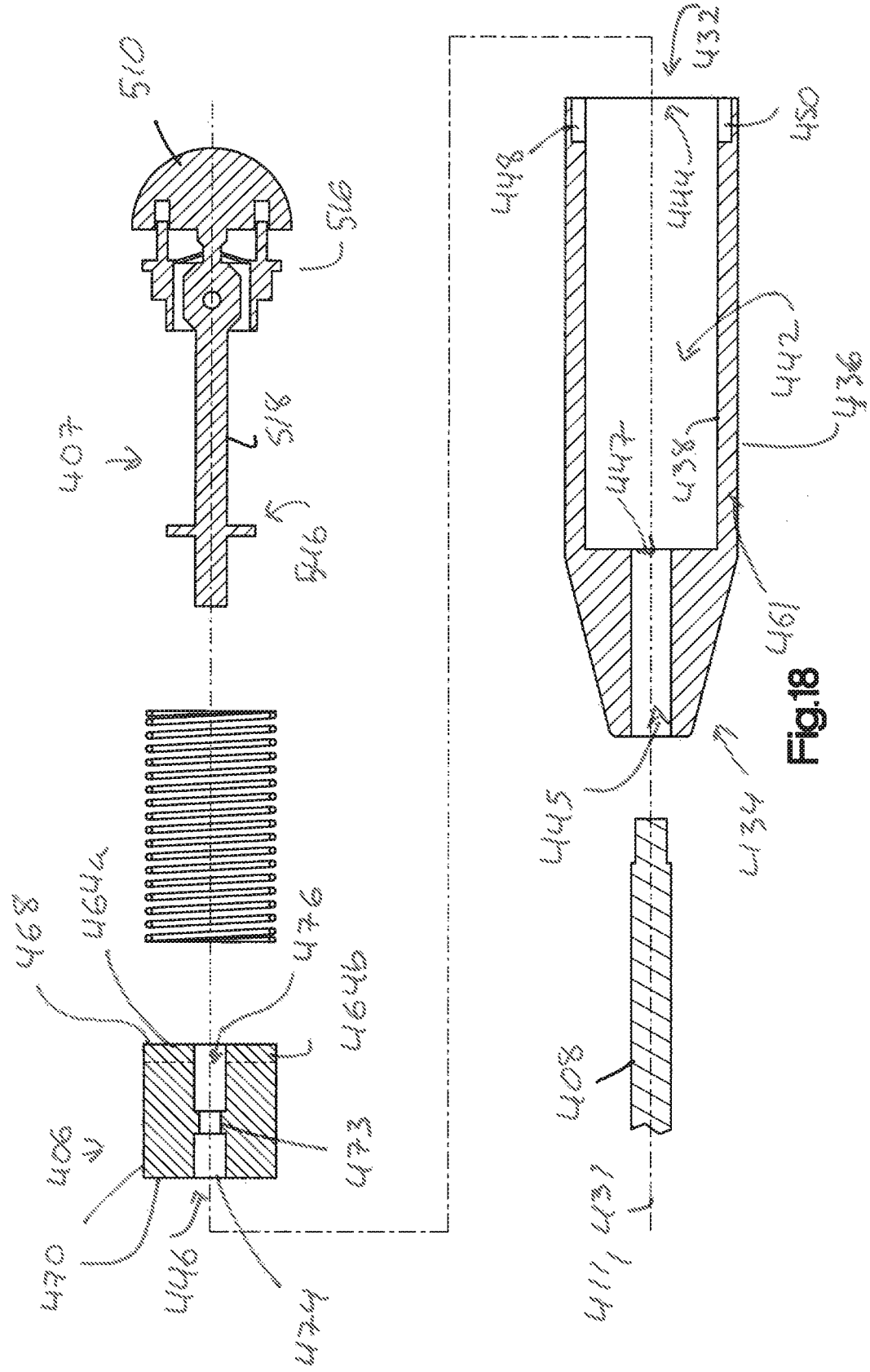

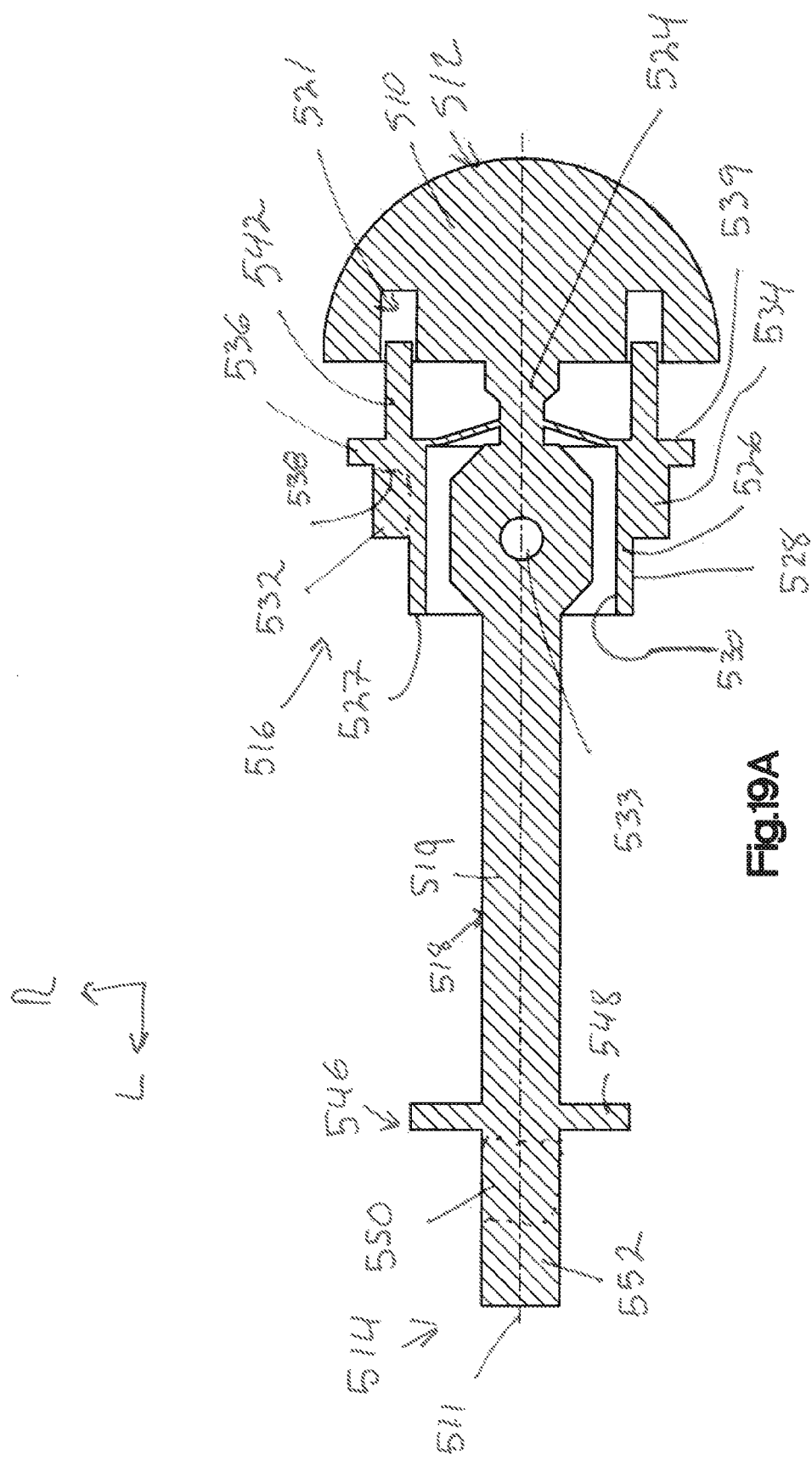

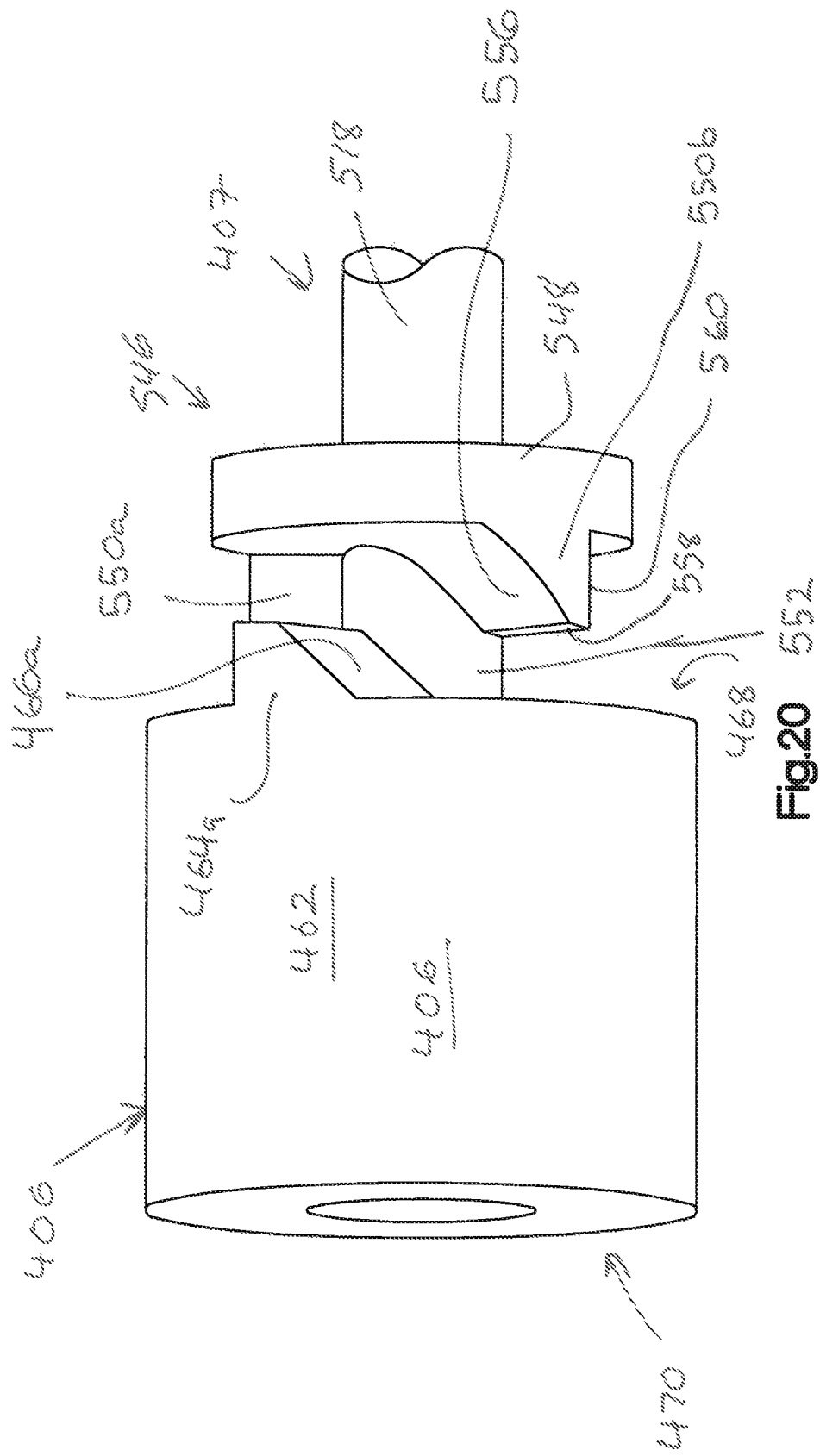

TORQUE LIMITING INSTRUMENT, SYSTEM AND RELATED METHODS

TECHNICAL FIELD

The present disclosure relates to a torque limiting instrument, system and related methods, and particularly to a torque limiting driving instrument and system, a method of making same, and a method for limiting torque.

BACKGROUND

Surgical securement devices, such as anchors or screws, that fix implants to bone or other tissue are effective when used consistently with clinically tested protocols. Torque limiters are one type of device that surgeons can use to help position and appropriately lock an anchor in place. Torque limiters can help ensure that only the torque required to secure the implant in position is actually applied to the anchor during implantation. Torque limiters also help limit damage to the anchor or the tissue. Despite the use of torque limiters for medical applications, typical torque limiter designs are complex and costly to manufacture.

SUMMARY

An embodiment of the present disclosure relates to a method for limiting torque that is transferred from a handle end of a driving instrument through a torque transfer member to a shaft that extends relative to the handle. The method can include applying a torque to the handle along a direction relative to the shaft and transmitting the applied torque from the handle through the torque transfer member to the shaft when the applied torque is less than a limited torque value. When the applied torque is greater than the limited torque value, at least one of the torque transfer member and the handle deforms to allow the handle to rotate along the direction relative to both the torque transfer member and the shaft.

BRIEF DESCRIPTION OF THE DRAWINGS

The foregoing summary, as well as the following detailed description of illustrative embodiments of the instrument of the present disclosure, will be better understood when read in conjunction with the appended drawings. It should be understood, however, that the application is not limited to the precise schematics and arrangements shown. In the drawings:

FIG. 5A is side elevation view of a handle of the instrument shown in FIG. 1;

FIG. 5B is cross-sectional view of the handle taken along line 5B-5B in FIG. 5A;

FIG. 5C is a detailed cross-sectional view of a portion of the handle shown in FIG. 5B;

FIG. 6A is a side elevation view of a torque transfer member of the instrument shown in FIG. 1;

FIG. 6B is a cross-sectional view of the torque transfer member taken along line 6B-6B in FIG. 6A;

FIG. 7 is a side view of the instrument shown in FIG. 1;

FIG. 8A is a cross-sectional view of the instrument taken along line 8A-8A in FIG. 7;

FIG. 8B is a detailed sectional view of a portion of the handle shown in FIG. 8A;

FIGS. 9A and 9B are schematic cross-sectional views of a portion of the instrument in FIG. 1 illustrating the handle in a first or initial configuration;

FIGS. 10A and 10B are schematic cross-sectional views of a portion of the instrument illustrated in FIG. 1, illustrating the handle in a second deformed configuration;

FIG. 12 is an exploded view of the instrument shown in FIG. 11;

FIG. 13 is an exploded cross-sectional view of the instrument shown in FIG. 11;

FIG. 14 is a cross-sectional view of the instrument shown in FIG. 11;

FIG. 16 is a cross-sectional view of an instrument, according to another embodiment of the present disclosure;

FIG. 18 is an exploded cross-sectional view of the instrument shown in FIG. 16;

FIGS. 19A and 19B are section views of the actuator in the instrument shown in FIG. 16 illustrating an initial configuration and a deformed configuration; and FIG. 20 is a perspective view of a torque transfer member and an actuator used in the instrument shown in FIG. 16.

DETAILED DESCRIPTION OF ILLUSTRATIVE EMBODIMENTS

Figure 1:
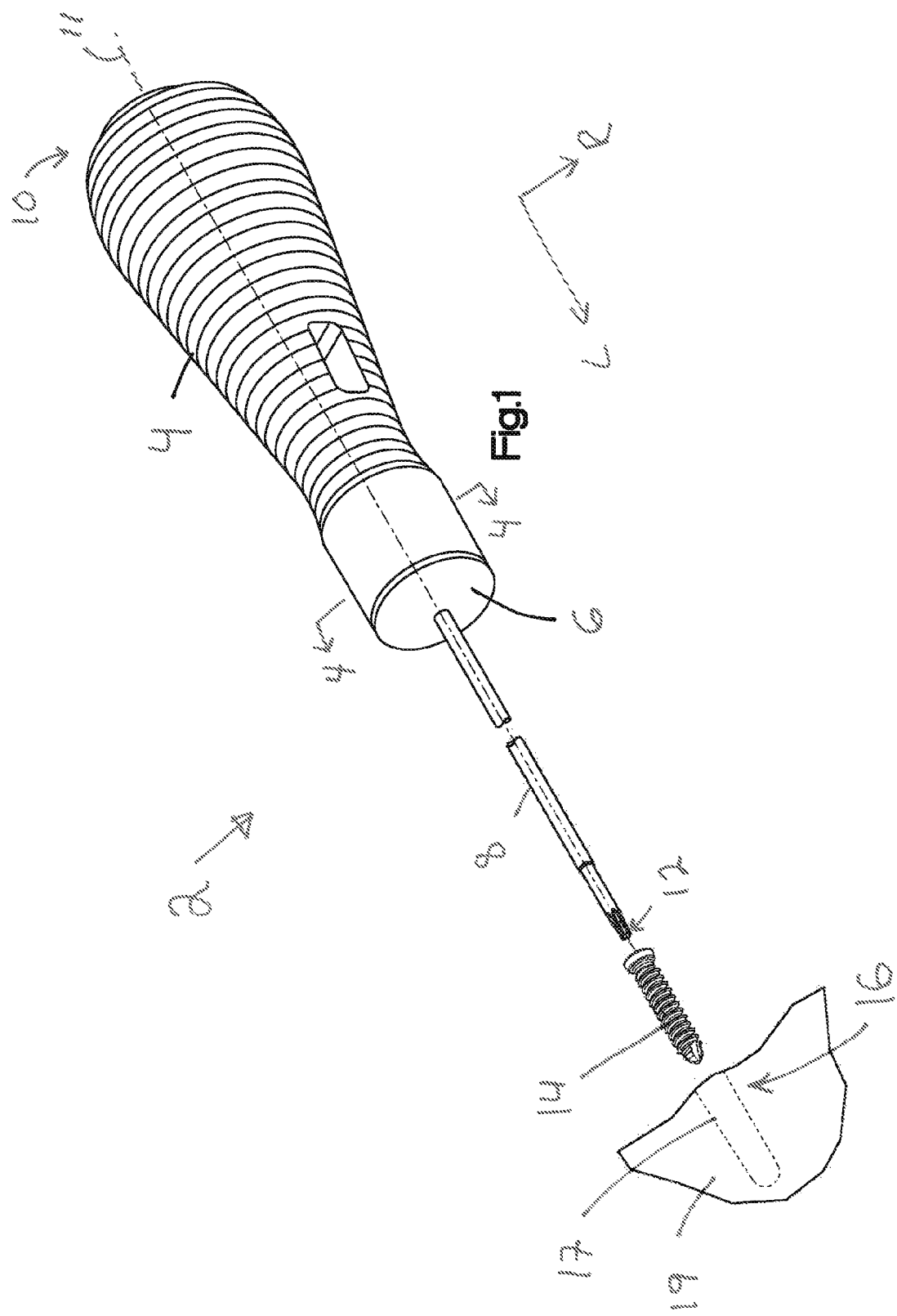
FIG. 1 is a perspective view of a torque limiting instrument, according to an embodiment of the of the present disclosure.

Referring to FIG. 1, a torque limiting driving instrument or instrument 2 can receive or support a fastener 14 and can secure the fastener 14 into a fastening location 16 up to a specified torque limit or a limited torque value TL. The instrument 2 can include a handle 4, a torque transfer member 6 rotatably coupled to the handle 4, and a shaft 8 supported at least by the torque transfer member 6. For instance, the shaft 8 is attached to the torque transfer member 6 or is integral and monolithic with the torque transfer member 6. The instrument 2 extends between a proximal end 10, which can be defined by the handle 4, and a distal or fastener engaging end 12 that is spaced from the proximal end 10 along an instrument axis 11, which can extend along a longitudinal direction L or any other linear or nonlinear direction as desired. As used herein, the term "proximal" and derivatives thereof refer to a direction from the fastener engaging end 12 toward the proximal end. As used herein, the term "distal" and derivatives thereof refer to a direction from the proximal end 10 toward the fastener engaging end 12.

The shaft 8 extends relative to the handle 4 along the instrument axis 11 toward the fastener engaging end 12. When a torque applied (also referred to as an applied torque TA herein) to the handle 4 along a first rotation direction 3 (FIG. 5) is less than the limited torque value TL, the applied torque TA is transferred through the torque transfer member 6 to the shaft 8 and the instrument 2 drives the fastener 14 into the fastening location 16. When the applied torque TA on the handle 4 is greater than the limited torque value TL, at least one of the torque transfer member 6 and the handle 4 can elastically deform to allow the handle 4 to rotate along the rotation direction 3 relative to both the torque transfer member 6 and the shaft 8. When the handle 4 rotates relative to both the torque transfer member 6 and the shaft 8, further rotation or tightening of the fastener 14 along rotation direction 3 into the fastening location 16 is limited because torque is no longer transferred to the fastener 14 via the shaft 8. Deformation of the handle 4 and/or torque transfer member 6 occurs along a fixed position on the instrument axis 11 such that neither the handle 4 nor the torque transfer member 6 are longitudinally displaced to limit the torque transferred to the shaft 8. Further, the instrument is configured to limit torque when the handle 4 is rotated along a first rotation direction 3 as described above. When the handle 4 is rotated along a second rotation direction 5 that is opposite the first rotation direction, the instrument 2 does not include a torque limiting function. It will be appreciated by a person of ordinary skill that some fasteners are secured or tightened in position via clockwise rotation direction and other fasteners can be tightened in position via counter-clockwise rotation direction. Thus, the torque limiting instrument as described herein can be configured to limit the application of torque applied in whatever fastening direction that the fastener is configured for.

Figure 4:
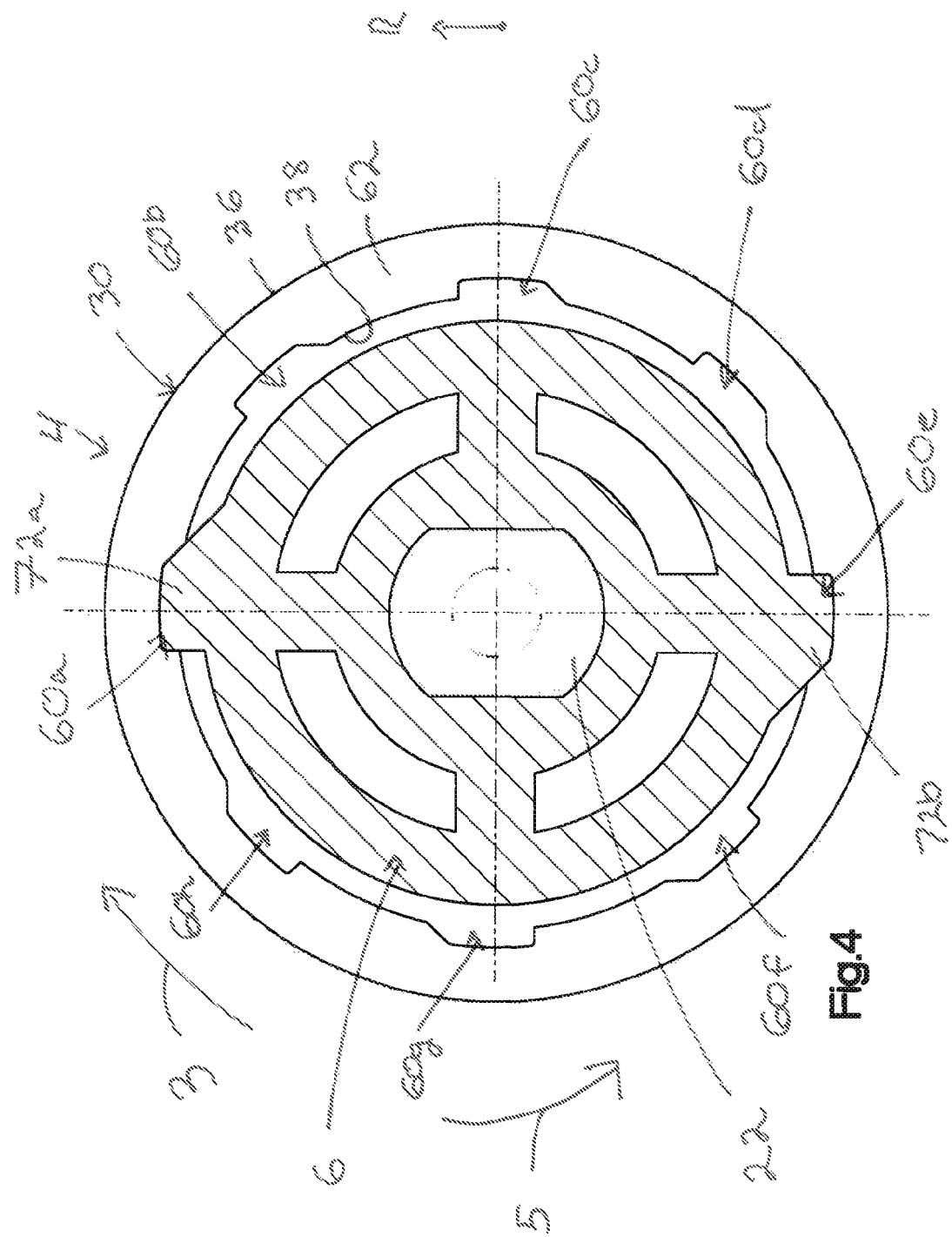
FIG. 4 is a cross-sectional view of the instrument taken along line 4-4 in FIG. 1.
Figure 15A:
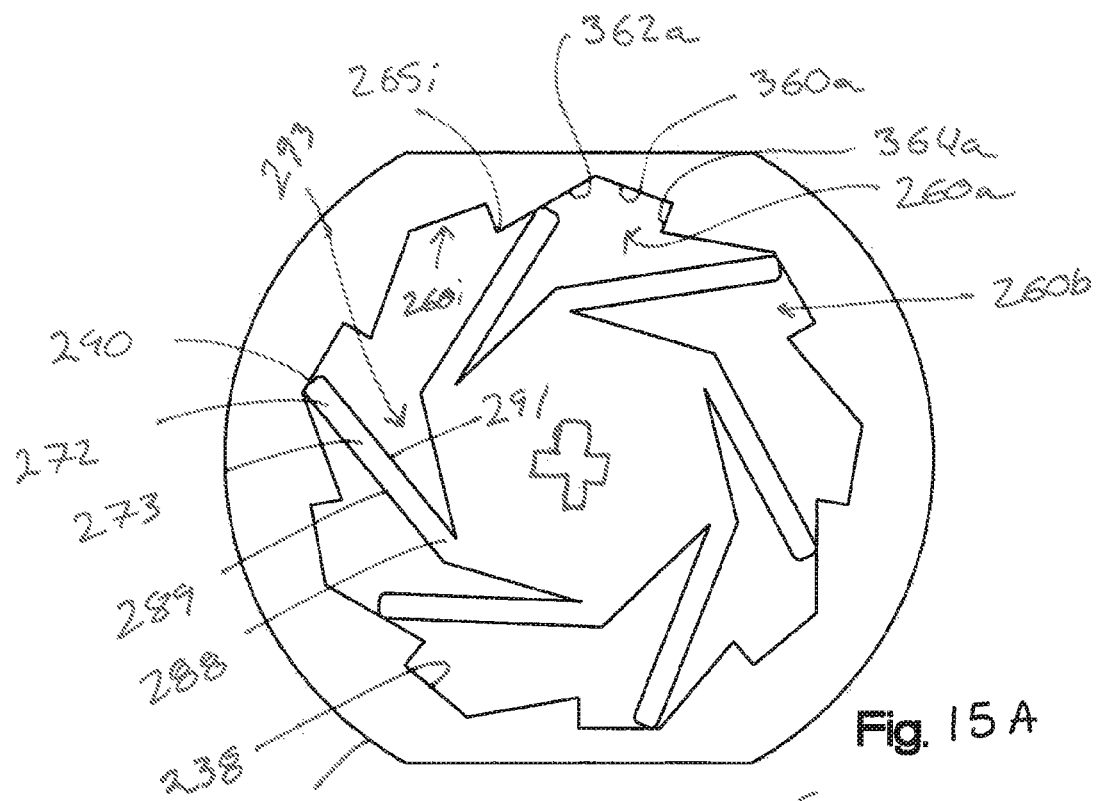
FIGS. 15A and 15B are cross-sectional view of a portion of the instrument shown in FIG. 11, illustrating the torque transfer member in first configuration and a second deformed configuration.
Figure 15B:
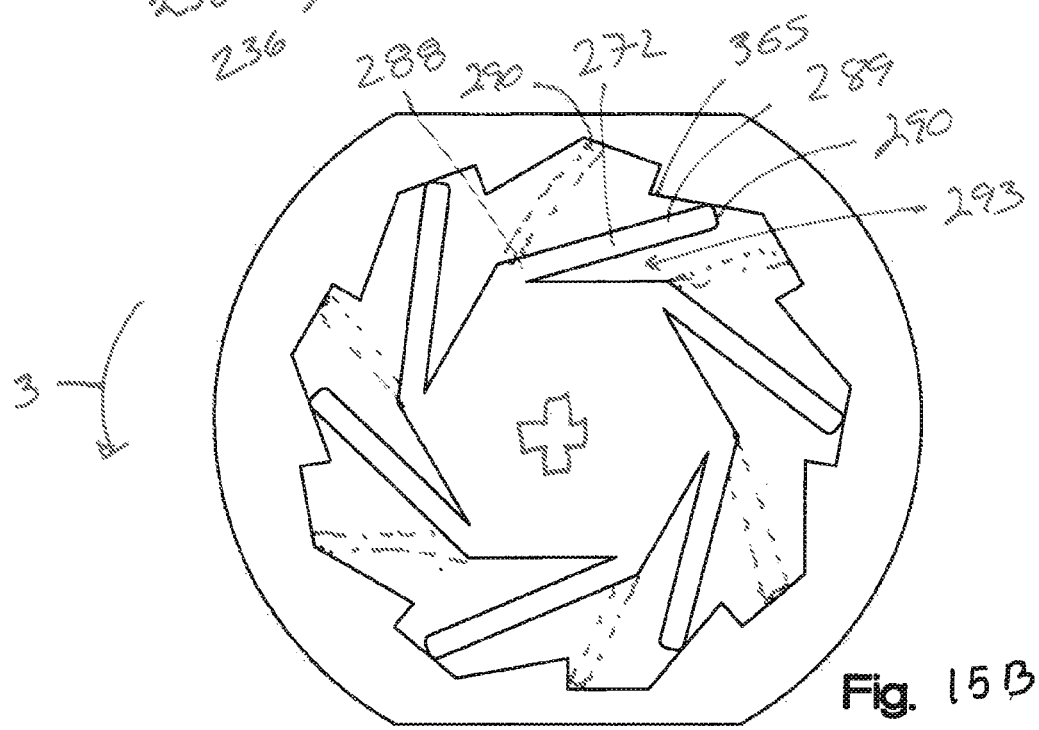

The instrument 2 is configured such that the handle 4 or the torque transfer member 6 can cyclically iterate between a first configuration X (FIG. 4, 15A) and a second or deformed configuration Y (FIG. 10A, 10B, 15B). The first configuration X is when the handle 4 and torque transfer member 6 are rotatably coupled such that the instrument 2 is capable of transferring the applied torque TA through the torque transfer member 6 to the shaft 8. The second or deformed configuration Y is when the applied torque TA exceeds the torque limited value TL, and either of the handle 4 or the torque transfer member 6 is deformed such that the handle 4 is de-coupled from the torque transfer member 6 and can rotate relative the torque transfer member 6 and the shaft 8. When the instrument 2 is in the second configuration Y and further torque is applied to the handle 4 along the rotation direction 3, the handle 4 continues to rotate relative to the torque transfer member 6 such that the instrument 2 is transitioned back into the first configuration X (FIG. 4, 15A). Iterations between the first and second configuration Y can cause an audible "click" alerting the user that the specified torque limit for the fastener 14 has been met. The instrument axis 11 is generally aligned with and extends along the instrument longitudinal direction L. The instrument 2 defines a radial direction R that is oriented perpendicular to the longitudinal direction L and/or the instrument axis 11. The radial direction R can be oriented along a transverse direction T that is perpendicular to the longitudinal direction L and/or the instrument axis 11, a lateral direction A that is perpendicular to both the radial direction R and the longitudinal direction L and/or the instrument axis 11, or a combination of the lateral A and transverse T directions. Thus, while the instrument 2 is illustrated as having radial coordinates, the instrument can alternatively be constructed so as to define Cartesian coordinates, such that the radial direction R defines one or both of lateral A and transverse T directions.

The fastener engaging end 12 is configured to receive, engage or support the fastener 14. The fastener 14 can be any type of fastener for instance an anchor, screw, bolt, or threaded shaft. The fastening location 16 can be a bore or cavity 17 in a bone 19, a bore and/or cavity in an implant, an additional fastener, for instance a nut or socket, self-drilling fasteners, or any other device or structure configured to receive a fastener. In a particular embodiment, the instruments as described herein are surgical driving instrument is used to implant anchors or screws into an implantable device, bone or other tissue.

Referring to FIG. 4, the handle 4 is configured for rotatable coupling to the torque transfer member 6. In the illustrated embodiment, the handle 4 can define a handle body 30 with one more longitudinally aligned grooves 60 that extend along a portion of the handle body 30. The torque transfer member 6 can define a body 70 that has one or more protrusions 72 that protrude from the body 70 along the radial direction R into coupling engagement with the grooves 60. The grooves 60 and protrusions 72 are configured to mate and couple with the corresponding structure of the other when the instrument 2 is in the first configuration X. When the instrument is in the second configuration Y, the protrusions 72 are decoupled from the grooves 60 so that the handle 4 is rotatable relative to the torque transfer member 6 and shaft 8.

Figure 2:
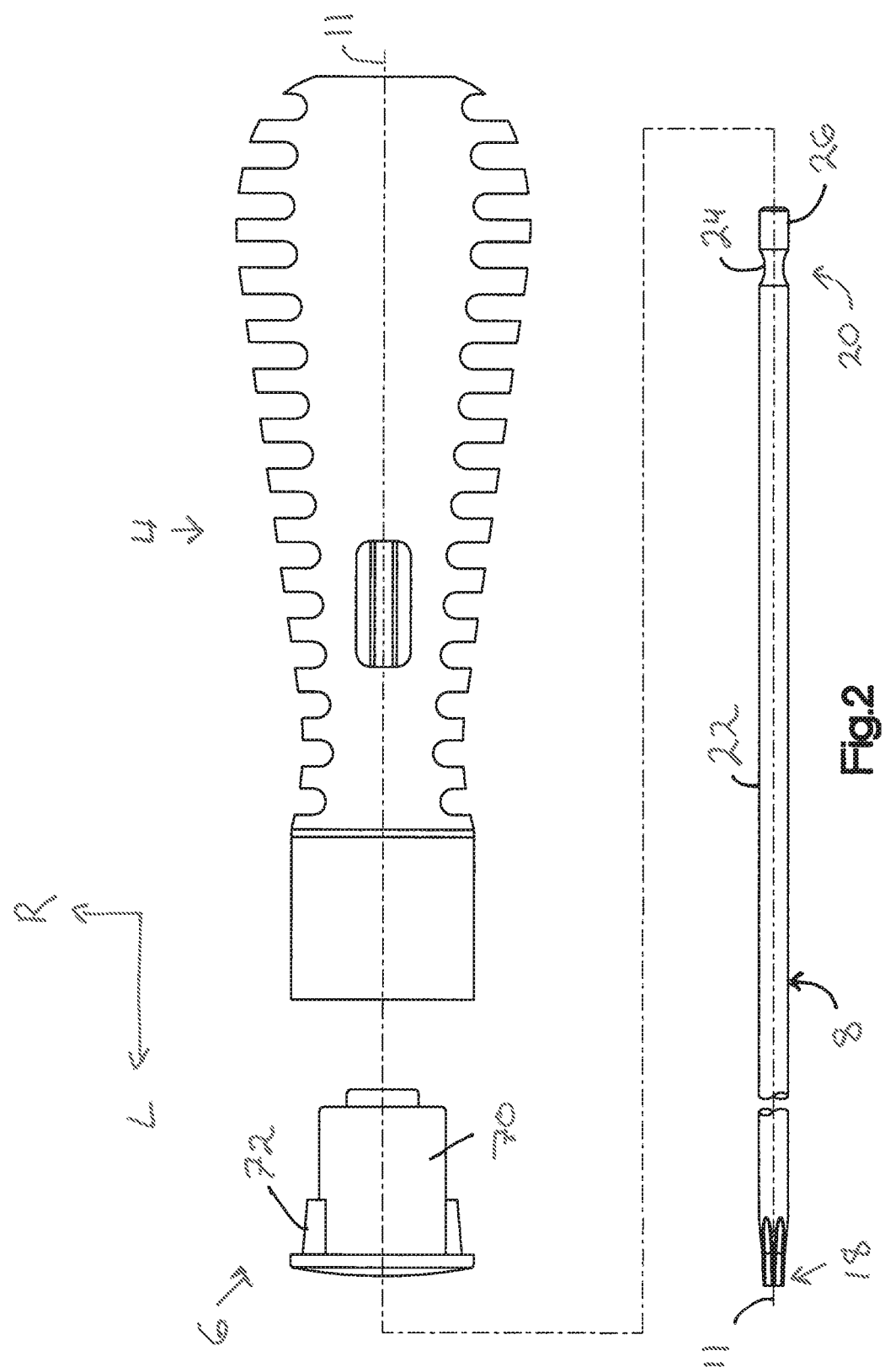
FIG. 2 is an exploded view of the instrument shown in FIG. 1.
Figure 3:
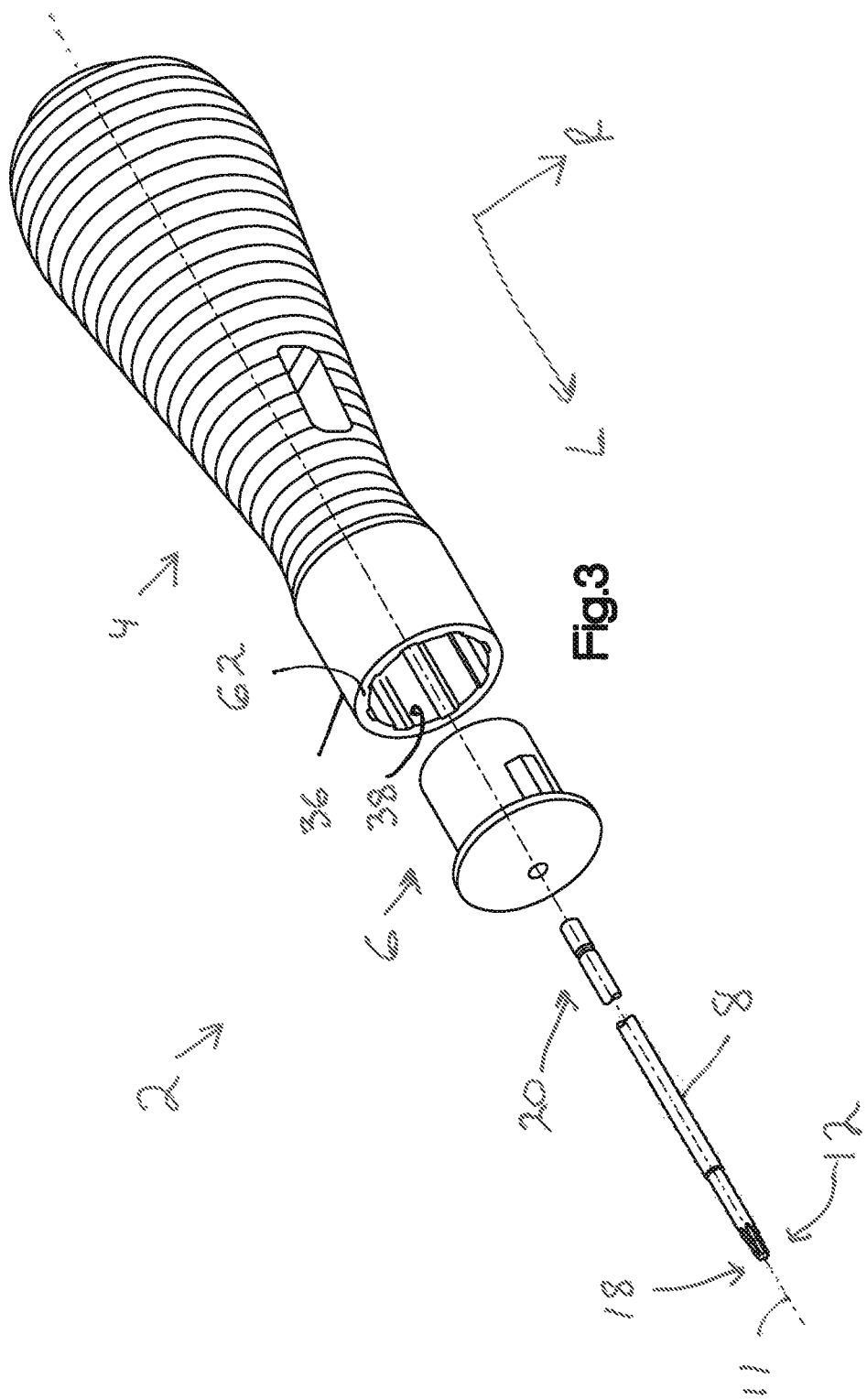
FIG. 3 is a perspective exploded view of the instrument shown in FIG. 1.

As shown in FIGS. 1, 2 and 7, at least a portion of the shaft 8 is fixed, for instance, rotationally fixed, to the torque transfer member 6. A portion of the shaft 8 can also be supported by handle 4. The shaft 8 can define a distal end 18, a proximal end 20 spaced proximally from the distal end 18 along the longitudinal direction L, and an intermediate portion 22 disposed between the shaft distal end 18 and proximal end 20. In the illustrated embodiment, the shaft distal end 18 forms the fastener engaging end 12 of the instrument 2, the intermediate portion 22 is supported by the torque transfer member 6, and the shaft proximal end 20 is carried by the handle 4 (FIGS. 7-8). The shaft distal end 18 can be configured in any manner so as to engage a fastener 14. The fastener engaging end 12 can define a hex tip, phillips, flat, star, socket, or any other suitable fastener attachment member. In another embodiment, the fastener engaging end 12 can be attached to the fastener attachment member. For instance, the fastener engaging end 12 can be coupled to a socket (FIG. 12) that defines the fastener attachment member. The socket can be configured to mate with a head of a fastener, for instance the head of an anchor or screw, or with a nut. Further, the shaft distal end 18 can be configured to have a modular design such that different engagement tips can be coupled to the shaft distal end 18 and used interchangeably. The shaft distal end 18 can be magnetized to support a fastener. The shaft intermediate portion 22 engages the torque transfer member 6 such that the torque transfer member is rotationally fixed to the shaft 8. The shaft 8 can define a ridge 28 disposed between the shaft proximal end 20 and shaft distal end 18. The intermediate portion 22 is disposed proximally relative to the ridge 28 toward the shaft proximal end 20. The intermediate portion 22 can have a square, rectangular, or a cross-shaped cross-sectional dimension configured to mate with a corresponding structure in the torque transfer member 6. The cross-sectional dimension distal to the ridge 28 can be circular. The shaft proximal end 20 can define a neck 24 and an engagement member 26 extending from the neck 24. The shaft 8 can be formed of steel, stainless steel, metal or metallic alloy, or any other material having a sufficient strength and rigidity for use in a driving instrument. The handle 4 can receive the shaft engagement member 26 so that the handle 4 is rotatable with respect to the shaft.

Referring to FIGS. 5A-5C, the handle 4 can define a handle body 30 that extends between a handle proximal end 32 and a handle distal end 34 spaced apart from the proximal end 32 along the longitudinal direction L. The handle body 30 can further define a handle central axis 31 disposed at a radial center of the handle body 30. The handle axis 31 is coaxial with instrument axis 11. The handle body 30 can also define an outer surface 36, an inner surface 38 spaced apart from the outer surface 36 along the radial direction R, and a distal-facing surface 40 that extends from the inner surface 38 toward the handle central axis 31 along the radial direction R. A wall 62 extends between the handle outer surface 36 and the handle inner surface 38 along the radial direction R, and around a perimeter of the handle body 30. The inner surface 38 and the distally-facing surface 40 can define a cavity 42 that extends at least partially through the handle body 30 along the longitudinal direction L. The handle body 30 also defines a distal opening 44 in communication with cavity 42. The opening 44 is sized to receive at least a portion of the torque transfer member 6 therethrough. The cavity 42 is configured to rotatably couple the handle 4 to the torque transfer member 6, as further detailed below.

Referring to FIGS. 3 and 5A-5C, the handle body 30, for instance the wall 62 can define the grooves 60a-h. The grooves 60a-h are configured to correspond to the structure of the protrusions 72. The grooves 60a-h extend along the longitudinal direction L (FIG. 3) from the handle distal end 34 toward the distal-facing surface 40. The grooves 60a-h can be linear grooves. The handle body 30 can define a first handle radial axis T1 extending through diametrically opposed grooves 60, for instance grooves 60a and 60e. The first radial axis is perpendicular to the handle axis 31. The handle body 30 also defines a second handle radial axis T2 extending between diametrically opposed grooves 60, for instance grooves 60c and 60g. The first radial axis T1 is perpendicular to the second radial axis T2. Each axes T1 and T2 intersects the handle axis 31 or radial center C of the handle body 30.

Referring to FIGS. 5B and 5C, the wall 62 defines each groove 60 such that the groove 60 extends along the radial direction R toward the outer surface 36. The inner surface 38 also defines inner radial surfaces 166a-h disposed between each groove 60. The inner radial surfaces 166a-h can also be referred to as the terminal ends of the wall projections 64. The handle inner surface 38 can define one or more outer radial surfaces 160 that define the outer-most radial boundary of the respective one or more grooves 60. The outer radial surfaces 160 can be disposed between a first wall 162 and a second wall 164 opposite the first wall 162. The first and second walls 162 and 164, and the outer radial surface 160 at least partially define the groove 60. The first wall 162 extends from the outer radial surface 160 to a first inner radial surface 166a that is spaced apart from the handle outer surface 36 (and outer radial surface 160) along the radial direction R. The second wall 164 also extends from the outer radial surface 160 to the inner radial surface 166a. The first wall 162 is inclined toward the first rotation direction 3. Specifically, the first wall 162 is inclined at an angle α. Angle α is defined between a line 165 extending along the first wall 162 and the first radial axis T1. In the illustrated embodiment, angle α can vary between about 20 degrees and about 75 degrees. In an exemplary embodiment, angle α is about 45 degrees. The second wall 164 can be perpendicular to or have a slight inclination relative to the outer radial surface 160.

Continuing with reference to FIGS. 5B and 5C, the handle body 30 is dimensioned to facilitate deformation or iteration between the first and second configuration Y. The handle body 30 can define a first distance or groove pair distance A1 extending between opposing radial surfaces 160c and 160g of diametrically opposed respective grooves 60c and 60g. The handle body 30 can also define a second distance or handle outer diameter A2 that extends between a pair of opposing points 66a of 66b on the outer surface 36 that intersect the second radial axis T2. The difference between A1 and A2 can define a wall groove thickness W1. The handle body 30 can also define a third distance or projection pair inner diameter A3 that extends between a pair of points 67a, 67b on the inner surfaces 166b and 166f of the handle 4. The difference between distances A2 and A3 can define a wall projection thickness W2. The difference between the W2 and W1 defines the groove depth W3 along the radial direction R. Distances A1, A2 and A3 can vary as needed and are selected to conform with the corresponding dimensions of the torque transfer member 6. In an embodiment, the first distance A1 can range between about 14 mm and about 46 mm. The second distance A2 can range between about 18 mm and about 50 mm. The third distance A3 can range between about 12 mm and about 43 mm. The wall groove thickness W1, projection wall thickness W2, and groove depth W3 can vary as well with modifications to the distances A1, A2, and A3. In an instrument configured for 0.8 nM torque limit for instance, distance A1 can be 18.3 mm, distance A2 can be about 22 mm, and distance A3 can be 17 mm. In an instrument configured for a 4.0 nM torque limit, the distance A1 can be about 22 mm, distance A2 can be about 22 mm, and distance A3 can be about 20 mm.

Referring to FIG. 7-8B, the handle body 30 can be configured to receive a portion of the shaft 8 such that the handle 4 is rotatable relative to the shaft 8. In the illustrated embodiment, the handle body 30 defines a bore 46 that extends from the distal facing surface 40 toward the handle proximal end 32 along the longitudinal direction L. The bore 46 can extend partially through the handle body 30. The distal facing surface 40 defines an opening 47 in communication with the bore 46. The shaft 8 can pass through the opening 47 into the bore 46. The bore 46 and opening 47 can be coaxial with the handle axis 31 and instrument axis 11.

Referring to FIGS. 8A and 8B, the handle body 30 is configured to rotationally support a portion of the shaft 8. The handle body defines a ridge 55 that extends into the bore 46 along a radial direction R into the shaft neck 24. The shaft engagement member 26 is proximal to the ridge 55 to secure the longitudinal position of the shaft 8 in the bore 46. The ridge 55 abuts the shaft engagement member 26 so that the handle 4 can rotate about the shaft 8 when the applied torque exceeds the torque limit as described above.

Referring to FIGS. 4, 6A and 6B, the torque transfer member 6 is configured for rotatable coupling to the handle 4, and fixedly coupled to a portion of the shaft 8 such that the torque transfer member 6 and shaft 8 are rotatable together. The torque transfer member body 70 extends between a proximal end 74 and a distal end 76 spaced apart from the proximal end 74 along a longitudinal direction L. The body 70 defines a central axis 71 extending through the body proximal end 74 and body distal end 76. The central axis 71 is coaxial with the instrument axis 11 and aligned with the longitudinal direction L. The body 70 can also define a first radial axis M1 that extends along the radial direction R through the protrusions 72a and 72b, and a second radial axis M2 that extends along the radial direction R and is perpendicular to the first radial axis M1 and the central axis 71. A circumferential ledge 78 extends from the body 70 along the radial direction R and has a proximal facing surface 79 configured to abut the d 63 of the handle body 30. The body 70 can define a proximal protrusion 75 that is configured for insertion into the opening 47 of the handle body 30. The body 70 is configured to fixedly support the shaft 8, for instance the intermediate portion 22 of the shaft 8. The body 70 defines a bore 82 extending between the proximal end 74 and the distal end 76 of the body 70 along the central axis 71. The bore 82 is configured to fixedly receive at least a portion of the shaft 8 therethrough. The cross-sectional shape of the bore 82 can correspond to the cross-sectional shape of the intermediate portion 22 of the shaft 8 such that the torque transfer member 6 is not rotatable about the shaft 8 when the instrument is assembled as shown in FIG. 8. For instance, the cross-sectional shape of the bore 82 can be square, rectangular, or a cross-shaped.

In a particular embodiment as shown in FIG. 6B, the body 70 can define a shaft support member 85 which includes the bore 82. The body 70 can have an inner surface 81 spaced apart from the outer surface 80 along the radial direction R so as to define wall 83 extending between the outer surface 80 and inner surfaces 81. The body 70 includes struts 84a-84d that extend from the wall 83 along the radial direction R toward the central axis 71 to support the shaft support member 85. The struts 84a and 84c are generally aligned with the first transverse axis M1 while the struts 84b and 84d are aligned with the second radial axis M2. In the illustrated embodiment, the shaft support member 85 defines the proximal protrusion 75. The bore 82 is axially aligned with the handle body bore 46 so that the shaft 8 is at least partially received by the bores 82 and 46.

Referring to FIGS. 4, 6A and 6B, the one or more protrusions 72 project from the body 70 along a radial direction R and extend into coupling corresponding grooves 60 of the handle 4. The one or more protrusions 72 can include a first protrusion 72a that protrudes from the body 70 along the radial direction R, and a second protrusion 72b that protrudes from the body 70 along the radial direction R. The first protrusion 72a is illustrated diametrically opposed relative to the second protrusion 72b. The protrusions 72 can have other circumferential spacing as needed. The first and second protrusions 72a and 72b are received in opposing respective grooves 60. For instance, the first and second protrusions 72a and 72b are received in respective groove pairs 60a and 60e as shown in FIG. 4. The first and second protrusions 72a and 72b are disposed along first radial axis M1. The one or more protrusions 72 can also extend along the outer surface 80 of the body 70 along the longitudinal direction L at least partially between the body proximal end 74 and the body distal end 76. For instance, the protrusion 72 can extend from the ledge 78 to an end 89, which can define a protrusion length L1. The length L1 can range between 5 mm and 10 mm. In an exemplary embodiment of instrument configured for a 0.8 Nm torque limit value, the length L1 can be about 6.8 mm. In an exemplary embodiment of instrument configured for a 4.0 Nm torque limit value, the length L1 can be 8.1 mm. The protrusions 72 can also extend along the longitudinal direction L between the body proximal end 74 and the body proximal end 74. For instance, protrusion 72 can extend from the ledge 78 to the body proximal end 74. While a pair of protrusions 72a and 72b are shown, more than two protrusions 72 can be used. For instance, the protrusions 72 can be a plurality of flexible tabs (FIG. 14).

With reference to FIGS. 4 and 9A, each protrusion 72 can also define a first wall 88, an outer protrusion surface 90 spaced apart from the outer body surface 80 along the radial direction R, and a second wall 92 that extends from the outer surface 80 toward the protrusion surface 90 along the radial direction R. The first wall 88 is inclined to mate with the first wall 162 of the groove 60. The first wall 88 is inclined at an angle β defined between 1) a line extending along the first wall 88, and 2) the first radial axis M1. In an embodiment, angle β is substantially equal to angle α. The second wall 92 can be perpendicular to the body 70 or inclined slightly relative to the body in any direction. The torque transfer member 6 can define a first or outer member distance B1 that extends between opposing protrusion surfaces 90a and 90b along axis M1. The outer distance B1 can range between about 15 mm and about 25 mm, but such distance is not so limited. The distance B1 is less than or about equal to the groove pair distance A2 and greater than the projection pair distance A3 so that the protrusions 72 can deflect the wall 62 when the handle rotates (FIGS. 10A and 10B). The body 70 can also define a second body outer distance B2. The second body outer distance B2 can range between about 17 mm and about 23 mm, but such distance is not so limited. In an instrument configured for 0.8 nM torque limit for instance, distance B1 can be 18.3 mm, distance B2 can be about 16 mm. In an instrument configured for a 4.0 nM torque limit for instance, distance B1 can be about 21.9 mm, distance B2 can be about 18.5 mm. The particular dimensions B1 and B2 are such that the torque transfer member 6 frictionaly fits with the handle 4.

Referring to FIGS. 9A-10B, the first configuration X refers to when the members pairs 72 are coupled to the corresponding grooves 60 and the second configuration Y refers to when handle 4 is deflected so that the pair of protrusions 72 are decoupled from the grooves 60 and handle 4 is rotatable about the torque transfer member 6. In the first configuration X shown in FIG. 4, the protrusion pairs 72a and 72b are coupled to the corresponding pair of grooves 60a and 60e. The first inclined walls 88a, 88b are in slidable engagement with the respective groove inclined walls 162a, 162e of the groove pairs 60a and 60e. The second protrusion walls 92a and 92b are in an abutting relationship with the respective second groove walls 164a and 164e of the grooves 60a and 60e. When the handle 4 is rotated in the first rotation direction 3, the first inclined walls 88a and 88b bear against the groove inclined walls 162a and 162e until the applied torque on the handle 4 is greater than the torque limited value TL. When the applied torque is greater than or equal to the torque limited value TL, the protrusion pairs 72a, 72b can slide along the groove inclined walls 162a, 162e causing the handle body 30 to deform into the second deformed configuration Y as shown in FIGS. 10A and 10B. As the handle 4 further deforms, the protrusion pairs 72a, 72b slide into abutting relationship with the handle body inner radial surfaces 166a and 166e deforming the handle 4 into the second deformed configuration Y. Further rotation of the handle 4 in the rotation direction 3 causes the protrusion pairs 72a and 72b to slip into the adjacent grooves 60b and 60f (not shown), respectively.

The handle body wall 62 can define a circular cross-sectional dimension when the handle 4 is in the first configuration X as shown in FIG. 4. When the handle 4 is deformed into the second configuration Y the wall 62 is deflected or deformed into a generally elliptical cross-sectional dimension having the dimensions Q and Z as shown in FIG. 10A. Accordingly, when handle 4 is rotated so that the protrusions 72 and grooves are coupled again, the handle body wall 62 substantially recovers to the initial circular cross-sectional dimension.

In an embodiment, the handle, the torque transfer member, or both the handle and the torque transfer member are configured to resist a certain amount of applied torque.

When the applied torque TA reaches a limit, either the handle 4 or the torque transfer member 6 can radially deform so that either the handle or torque transfer member 6 are rotatable relative to the other. For instance, when the applied torque TA reaches a limit, the handle 4 can radially expand so that that handle 4 rotates relative the torque transfer member 6. In other embodiments, when the applied torque TA reaches a limit, the torque transfer member 6 can radially deform so that handle 4 can rotate relative to the torque transfer member 6.

The handle 4 and torque transfer member 6 can be formed of polymeric materials. Such polymeric materials can be thermoplastic or thermosets. Further, the polymeric materials can be blends of one or more polymers. Additional additives, such as hardeners, molecular weight extenders, pigments, fillers, lubricants, viscosity modifiers, etc., may be incorporated with one or more polymeric materials. Polymeric materials that can be used to form the handle 4 and/or the torque transfer member 6 include polyimide, polyamide, polycarbonate, polyethylene, high molecular weight polyethylene, ultra high molecular weight polyethylene, low density polyethylene, linear low density polyethylene, polypropylene, polyethylene terephthalate, polylactic acid, polyglycolic acid, polyglycolic-lactic acid, polyetherketones (PEK) such as polyetheretherketone (PEEK) and polyetherketoneketone (PEKK), as well as a co-polymers of any of the these polymers, silicones and derivatives thereof. In one embodiment, the handle 4 and torque transfer member 6 can be formed of the same polymeric material. In alternative embodiments, the handle 4 is formed from a first polymeric material, and the torque transfer member 6 is formed from a second polymeric material that is different from the first polymeric material. Further, either the handle 4 or the torque transfer member can be formed of metallic materials and the other of the handle 4 and torque transfer member 6 can be formed of a polymeric materials. The metallic materials can be steel, stainless steel, aluminum, or any metallic alloy.

The embodiment shown in FIGS. 1-10B is described such that the handle 4, or wall 62 deforms relative to the torque transfer member 6, such that the protrusions 72 decouple from the grooves 60. In other embodiments, the projections 64 can be elastically compressible to selectively decouple the handle 4 from the torque transfer member 6. For instance, the protrusion pairs 72a, 72b can be elastically compressible to decouple from the grooves 260 when the applied torque is greater than a torque limit value. In still other alternative embodiments, the torque transfer member 6 can deform and recover relative to the handle 4. For instance, the torque transfer member 6 can be radially compressed along the first radial axis T1 so that the protrusion pairs 72a, 72b are decoupled from the grooves 60, for example as shown in FIGS. 11-15B and detailed below. Further, it will be appreciated that the instrument 2 can be configured such that the handle 4 is partially inserted into a cavity formed by the torque transfer member 6. For instance, the handle 4 can include the protrusion pairs 72 while the torque transfer member 6 can include the grooves 60/projections 64 for coupling to the protrusions 72. Thus, either handle 4 can be configured to limit torque or the torque transfer member 6 can be configured to limit torque.

Referring to FIGS. 11-15B, in accordance with an alternative embodiment, the instrument 202 can include handle 204, a torque transfer member 206 coupled to the handle 204, and a shaft 208 support by the handle 204 and the torque transfer member 206. A cap member 207 is coupled to the handle 204 and engages the torque transfer member 206. For instance, the cap member 207 can hold the torque transfer member 206 in the handle 204. The instrument 202 defines a proximal end 210 and a distal or fastener engaging end 212 spaced apart from the proximal end 210 along an instrument axis 211. The shaft 208 is rotationally fixed to the torque transfer member 206 and extends relative to the handle 204 along the instrument axis 211 toward the fastener engaging end 212. In accordance with the alternative embodiment, when the torque applied to the handle 204 exceeds the torque limited value TV, a portion of the torque transfer member 206 is deformed to permit the handle 204 to rotate relative to the torque transfer member 206 and shaft 208. Specifically, the handle body 230 can define a plurality of grooves 260 extending along the longitudinal direction L of the handle 204. Further, the torque transfer member 206 defines a body 270 and a plurality of protrusions 272, for instance configured as flexible tabs 272a-272f, extend from the body 270 to couple with the corresponding number of grooves 260. The instrument 202 is configured to iterate between the first configuration X (FIG. 14, 15A) and the second configuration Y (shown in FIG. 15B). When the torque transfer member 206 is in the first configuration X, the flexible tabs 272 are biased or pre-stressed into engagement with the grooves 260. When the torque transfer member 206 and the second configuration Y shown in FIG. 15B (tabs shown in dashed lines), the flexible tabs 272a-f are decoupled from the grooves 260 so that the handle 204 is rotatable relative to the torque transfer member 206 and shaft 208.

Figure 11:
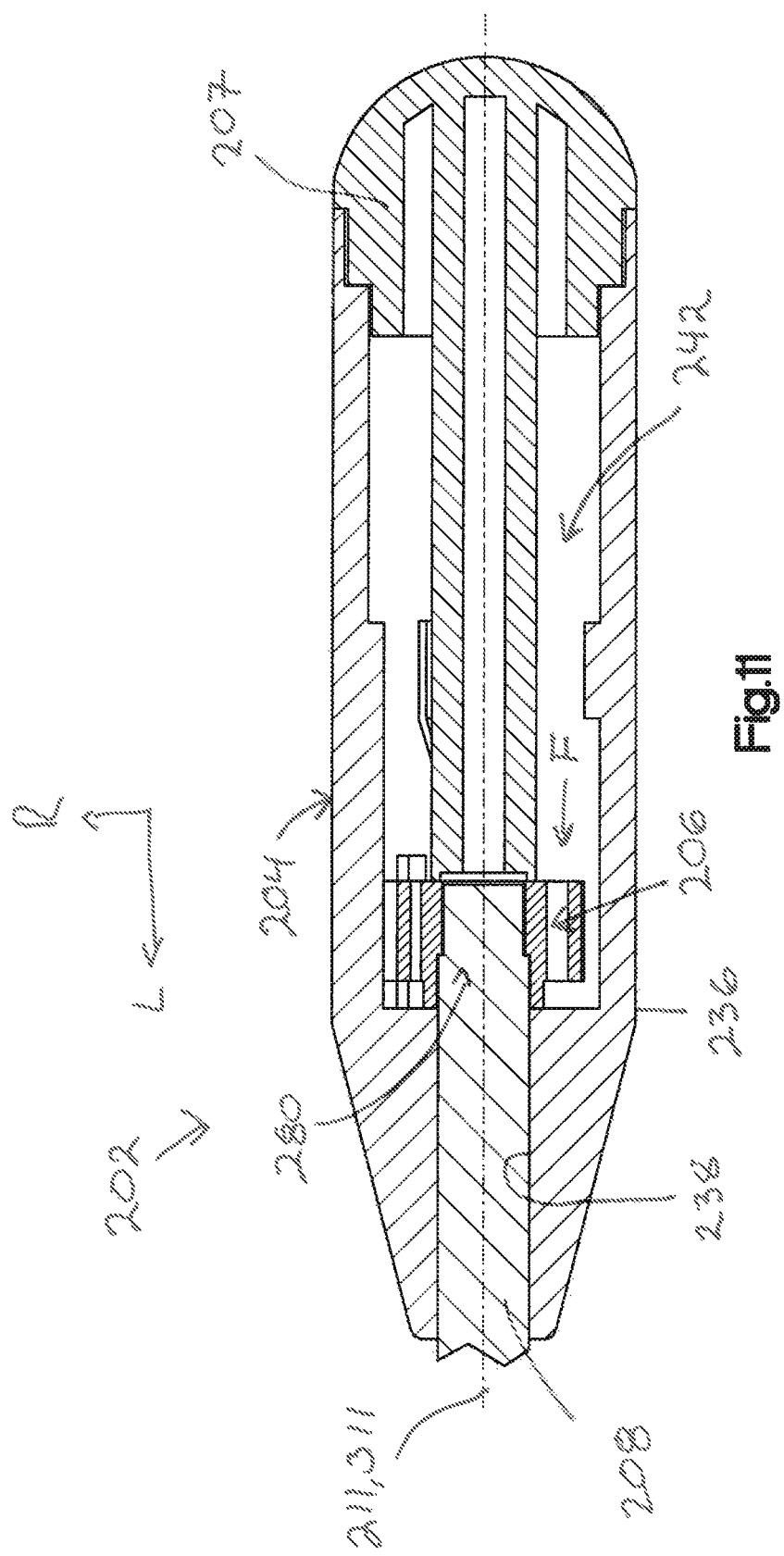
FIG. 11 is a cross-sectional view of an instrument according to another embodiment of the of the present disclosure.

As shown in FIGS. 11 and 12, the shaft 208 can define a distal end 218, a proximal end 220 spaced apart from the distal end 218 along the longitudinal direction L, and an intermediate portion 222 disposed between the shaft distal and proximal ends 218 and 220. In accordance with the alternative embodiment, the shaft distal end 218 forms the fastener engaging end 212 of the instrument 202, the intermediate portion 222 is supported by the handle 204 (FIG. 11), and the shaft proximal end 220 is rotationally fixed to the torque transfer member 206. The shaft distal end 218 can be configured as a socket 219 configured to receive a driving tip 221 therein. The shaft distal end 218 can be configured to engage a fastener 14. The shaft proximal end 220 can define engagement member 223 configured to mate with a corresponding structure in the torque transfer member 206. The engagement member 223 can have a cross-sectional shape in the form of a cross (FIG. 14). Other shapes are possible, such as a square, rectangular or partially linear cross-sectional dimension configured to mate with a corresponding structure in the torque transfer member 206. The engagement member 223 can define a tip 227. The shaft 208 can also define a ridge 228. The shaft intermediate portion 222 extends proximally from the ridge 228 to the engagement member 223. The shaft intermediate portion 222 has a first cross-sectional dimension 1C. The tip 227 has second cross-sectional dimension C2 that is less than the first cross-sectional dimension C1. The tip 227 can have the same cross-sectional shape illustrated as a cross-shape. The intermediate portion 222 can have a circular cross-sectional shape.

The handle 204 supports or carries the torque transfer member 206. Referring to FIGS. 12 and 13, the handle 204 can define a handle body 230 that extends between a handle proximal end 232 and a handle distal end 234 spaced apart from the proximal end 232 along the longitudinal direction L. The handle body 230 can further define a handle central axis 231. The handle axis 231 is coaxial with the instrument axis 211. The handle body 230 can also define an outer surface 236, an inner surface 238 spaced apart from the outer surface 236 along the radial direction R, and a proximal-facing transverse surface 240 that extends from the inner surface 238 toward the handle central axis 231 along the radial direction R. The handle body inner surface 238 and the proximal-facing surface 240 can define a cavity 242 that extends through the handle body 230 along the longitudinal direction L from the proximal-facing surface 240 toward the handle proximal end 232. The handle body 230 can define a proximal opening 244 in communication with the cavity 242, the opening 244 being sized to receive at least a portion of the cap member 207 therethrough. The cavity 242 is configured to couple handle 204 to the torque transfer member 206. Specifically, the inner surface 238 at the cavity 242 can define the plurality of grooves 260 alternating with a plurality of protrusions 265. Each groove 260 above includes radial surface 360 extending between a first wall 362 and a second wall 364. Adjacent walls 362 and 364 can intersect to define the protrusion 265. The intersection of the walls 362 and 364 can define a protrusion apex 365. The grooves 260 extend along longitudinal direction L of the handle 204. Further, the handle body 230 is configured to mate with a portion of the cap member 207. The proximal end 232 of the handle body 230 can define a pair detent sections 248 and 250 that extend from the inner surface 238 along the radial direction R at least partially into the handle body 230 toward the handle outer surface 236. In an alternative embodiment, the grooves 260 extend non-linearly along a portion of the handle 204 and gradually tapers into the handle body 230 (FIG. 12). During assembly of the instrument 202, the non-linear tapered grooves can guide the torque transfer member 206 toward the instrument proximal end 210 into position. Specifically, the torque transfer member 206 can be inserted into cavity 242. As the torque transfer member 206 is advanced along the longitudinal direction L, the tapered grooves engage the tabs 272. Further advancement of the torque transfer member 206 along the longitudinal direction L biases the tabs 272 further until the torque transfer member 206 is seated in the distal-most portion of the cavity and the tabs 272 are biased into the grooves 260. The cap member 207 can maintain the longitudinal position of the torque transfer member 206 in the handle 204.

The handle body 230 supports a portion of the shaft 208 such that the handle 204 is rotatable relative to the shaft 208. The handle body 230 can define a bore 246 distal to the cavity 242 that extends from the proximal-facing surface 240 to the handle distal end 234 along the longitudinal direction L. The proximal-facing surface 240 defines an opening 247 that provides a passage for the shaft 208 into the bore 246. The bore 246 and opening 247 can be aligned with the handle axis 231 and instrument axis 211. The bore 246 is configured to rotationally receive and carry a portion of the shaft 208 such that the handle body 230 can rotate about the shaft 208. For instance, the bore 246 can have a generally cylindrical cross-sectional dimension that is complementary to the intermediate portion 222 of the shaft 208. Accordingly, the bore 246 can rotationally receive and carry the intermediate portion 222 of the shaft 208 such that the handle body 230 can rotate about the shaft 208.

Referring to FIGS. 11-13, the cap member 207 can define a body 310 extending between a proximal end 312 and an opposed distal end 314. The body 310 can define an elongate member 315 that extends from the body 310 along the longitudinal direction L to the cap member distal end 314. The cap member distal end 314 can abut the proximal end 276 of the torque transfer member 206. The elongate member 315 can apply a force F to the torque transfer member 206 to maintain the torque transfer member 206 in a distal-most portion of the cavity 242. The cap member body 310 can define a wall 316 that extends between an outer surface 318 and an inner surface 320 spaced apart from the outer surface 318 along the radial direction R. The cap member body 310 can define a pair of slats 322 and 324 that protrude from the body 310 along the radial direction R. The slat pairs 322 and 324 are received in the detent section pairs 248 and 250 of the handle body 230 so that that cap member 207 is rotationally fixed within the handle body 230. Further, the cap member body defines a ledge 326 extending from the body 310 and forming a distal face 328 that can abut the proximal-most portion 263 of the handle body 230 when the instrument is assembled.

Referring to FIGS. 11-15B, the torque transfer member 206 is rotatably coupled to the handle 204 while rotatable fixed to shaft 208. The torque transfer member body 270 extends between a proximal end 276 and a distal end 278 spaced apart from the proximal end 276 along instrument axis 211. The body 270 can define a bore 280 extending through the body 270 between the proximal end 276 and the distal end 278. The bore 280 can define a first portion 282 and a second portion 284 proximal to the first portion 282. The bore 280 can have a cross-sectional shape that corresponds to the cross-sectional shape of the engagement member 223 of the shaft 208, and for instance, can have a cross-shape. The first bore portion 282 can receive the engagement member base 225 and the second bore portion 288 receives the engagement member tip 227. When the engagement member 223 is inserted into the bore 280, the torque transfer member 206 is rotationally fixed relative to the shaft 208 such that the torque transfer member 206 is prevented from rotating about the shaft 208.

The body 270 include multiple protrusions 272 configured as flexible tabs 272a-272f. The flexible tabs 272 are configured such that each 272 tab is compressed or biased when the torque transfer member 206 is positioned in the cavity 242 and received by the grooves 260. Each flexible tab 272a and 272f can define a tab body 273 that extends between a base 288 and an opposed free end 290 spaced apart from the base 288. The base 288 is adjacent to the torque transfer member body 270, while the free end 290 is offset from the body 270 along a radial direction R such that the tab 272 is inclined or angularly offset relative to the body 270. The tab body 273 can further define external surface 289 extending between the base 288 and free end 290 that faces the inner surface 238 of the handle body 270, and an opposed internal surface 291 that partially faces the body 270 and an adjacent tab 272. The body 270 and internal facing surface 291 define a gap 293 therebetween.

Referring to FIGS. 15A and 15B, the flexible tabs 272a-272f are configured to elastically flex so as to selectively couple and decouple from the respective grooves 260. The torque transfer member 206 can iterate between a first configuration X when the tabs 272 are moveable coupled to the grooves 260, and a second configuration Y when the flexible tabs 272 are deflected to de-couple from the grooves 260. When the torque transfer member 206 is in the first configuration X, the tabs 272 are in a compressed state in the cavity 242. That is, the tabs 272 are biased toward body 270 when coupled to the grooves 260. The degree of bias can affect the desired torque limit value. The more compressed or biased the tabs 272 when in the first configuration X, the higher the torque limit value can be. It will be appreciated that the tabs 272 can project into the grooves 260 in an unbiased configuration when in the first configuration X as well. The second configuration Y occurs when the torque transfer member 206 is radially deformed so as to allow rotation of the handle 204 relative to the torque transfer member 206. For instance, the flexible tabs 272a-272f are deflected to de-couple from the grooves 260. The handle 204 is rotatable about the torque transfer member 206 and the shaft 208 when the flexible tabs 272a-272f are flexed or deformed toward the body 270 to decouple from the grooves 260. When the handle 4 is rotated in the first rotation direction 3, the tab free ends 273 slide against the wall 362 as the applied torque increases. The tab free end 273 is urged, or deflected, toward the body 270 thereby decreasing the gap 293 such that the torque transfer member 206 is deformed into the second configuration Y. When the applied torque is greater than or equal to the torque limited value TL, the tab free end 273 slips past the apex 265 into the adjacent groove 260. The tab elastically recovers back into the first configuration X. Further rotation of the handle 4 along the rotation direction 3 guides the flexible tabs 272 into a set adjacent grooves 260. Rotation of the handle 4 in the second rotation direction 5 can cause the tab free ends 273 to abut the grooves 260 such that the handle 204, torque transfer member 206 and shaft 8 rotate together. That is, the instrument 202 is configured to limit torque along a first rotation direction that is the same rotation direction used to tighten a fastener into the fastening location.

In accordance with another alternative embodiment, the instrument is configured with a method of limiting torque. The instrument can be for instance a surgical driving instrument and configured according to the embodiments described above with respect to FIGS. 1-15B. The method can including applying a torque to the handle 4 along a rotation direction 3 relative to the shaft 8. Further, the applied torque can be transmitted from the handle 4 through the torque transfer member 6 to the shaft 8 when the applied torque is less than the limited torque value. The method can include deforming at least one of the torque transfer member and the handle when the applied torque is greater than the limited torque value. The torque transmission, and handle 4/torque transfer member 6 deformation can occur while the handle 4 and the torque transfer member 6 is stationary on the instrument axis 11 between an instrument proximal end 10 and the instrument distal end 12. In an embodiment, the handle 4 is deformed, while in other embodiments, the torque transfer member 6 is deformed.

The method can also include deforming the handle from a first configuration into a second configuration. In a an embodiment, the first configuration is defined as when the handle is not permitted to rotate relative to the torque transfer member and the shaft, and the second configuration is defined as when the handle is deformed so as to allow the handle to rotate along the direction relative to both the torque transfer member and the shaft. For instance, the deforming step can cause the protrusions to decouple from the grooves to permit the handle to rotate about the torque transfer member. Alternatively, the method of deforming can include deforming the torque transfer member from a first configuration into a second configuration. In another embodiment, the first configuration is when the handle is not permitted to rotate relative to the torque transfer member and shaft, and the second configuration is defined as when the torque transfer member is deformed so as to allow the handle to rotate along the direction relative to the torque transfer member and the shaft. For instance, the deforming step can cause a flexible tab to decouple from the at least one groove to permit the handle to rotate about the torque transfer member.

An embodiment of the present disclosure includes a method of producing a torque limiting driving instrument in accordance with the embodiments described above and illustrated in FIGS. 1-15B. The method can include the steps of forming the handle 4, 204, and forming the torque transfer member 6, 206. The method can also include forming the cap member 207 as described above and shown in FIGS. 11-13. The method can include compounding the polymer or polymers, additives, lubricants and other processing agents into a polymeric compound. The polymeric compound can be formed into the handle 4 (or 204) and torque transfer member 6 (or 206) by injection molding, reactive injection molding, blow molding, vacuum forming, thermoforming, additive machining, or laser sintering. A curing step can be included when the handle or torque transfer member is formed of a thermoset. The compounding and forming steps can occur separately and in sequence, or together in a single step. Further, when metallic materials form the handle or torque transfer member, CNC machining or other metal forming techniques may be used. The forming steps (whether with polymers or with metallic materials) include forming the handle and torque transfer member to have the respective structural details described above and shown in FIGS. 1-15B.

Further, the method of producing the instruments as can include assembling the handle, torque transfer member and shaft together to form an instrument with a specified torque limit. The method of producing can include attaching a shaft to a torque transfer member such that the shaft extends from the torque transfer member along an instrument axis 11. The method can also include attaching the torque transfer member to the handle. Attaching the torque transfer member to the handle includes inserting the torque transfer member into the handle cavity. In accordance with alternative embodiments, the method can include inserting the handle into a torque transfer member cavity. Further, the method can include packaging the instrument. Packaging can include placing the instrument into a sterile container, such as a polymeric bag, a carton, or other packing material.

Referring to FIGS. 16-19B, in accordance with an alternative embodiment, the instrument 402 can include a handle 404, a torque transfer member 406 coupled to the handle 404, and a shaft 408 supported by the handle 404 and the torque transfer member 406. The instrument can further include an actuator 407 that includes a moveable torque actuation member 546. The torque actuation member 546 is configured to move or deflect along the longitudinal direction L relative to the handle 404 and torque transfer member 406. When the actuator 407 is coupled to the handle 404, the torque actuation member 546 can deflect into and out of rotatable coupling with the torque transfer member 406 as further detailed below. Similar to the embodiments described above with respect to FIGS. 1-15, the instrument 402 can define a proximal end 410 and a distal or fastener engaging end 412 spaced apart from the proximal end 410 along an instrument axis 411. The instrument axis 411 is aligned with and extends along an instrument longitudinal direction L. The shaft 408 extends relative to the handle 404 along the instrument axis 411 toward the fastener engaging end 412 and can be rotationally fixed to the torque transfer member 406. In accordance with the alternative embodiment, the actuator 407 is configured to iterate the instrument 402 between 1) an inactive configuration, wherein the handle 404 is rotatable relative to the torque transfer member 406 and the shaft 408 and the instrument 402 has limited ability to drive a fastener 14 into the fastening location 16, and 2) an active configuration wherein the handle 404 is rotatable with the torque transfer member 406. Further, when the instrument 402 is in the active configuration, a torque applied TA to the handle 404 is transferred through the torque transfer member 406 to the shaft 408 when the applied torque is less than a limited torque value TV. When the applied torque TA is greater than the limited torque value TV, the torque transfer member 406 and the torque actuation member 546 decouple, thereby allowing the handle 404 to rotate with respect to the torque transfer member 406 and the shaft 408.

Figure 17:
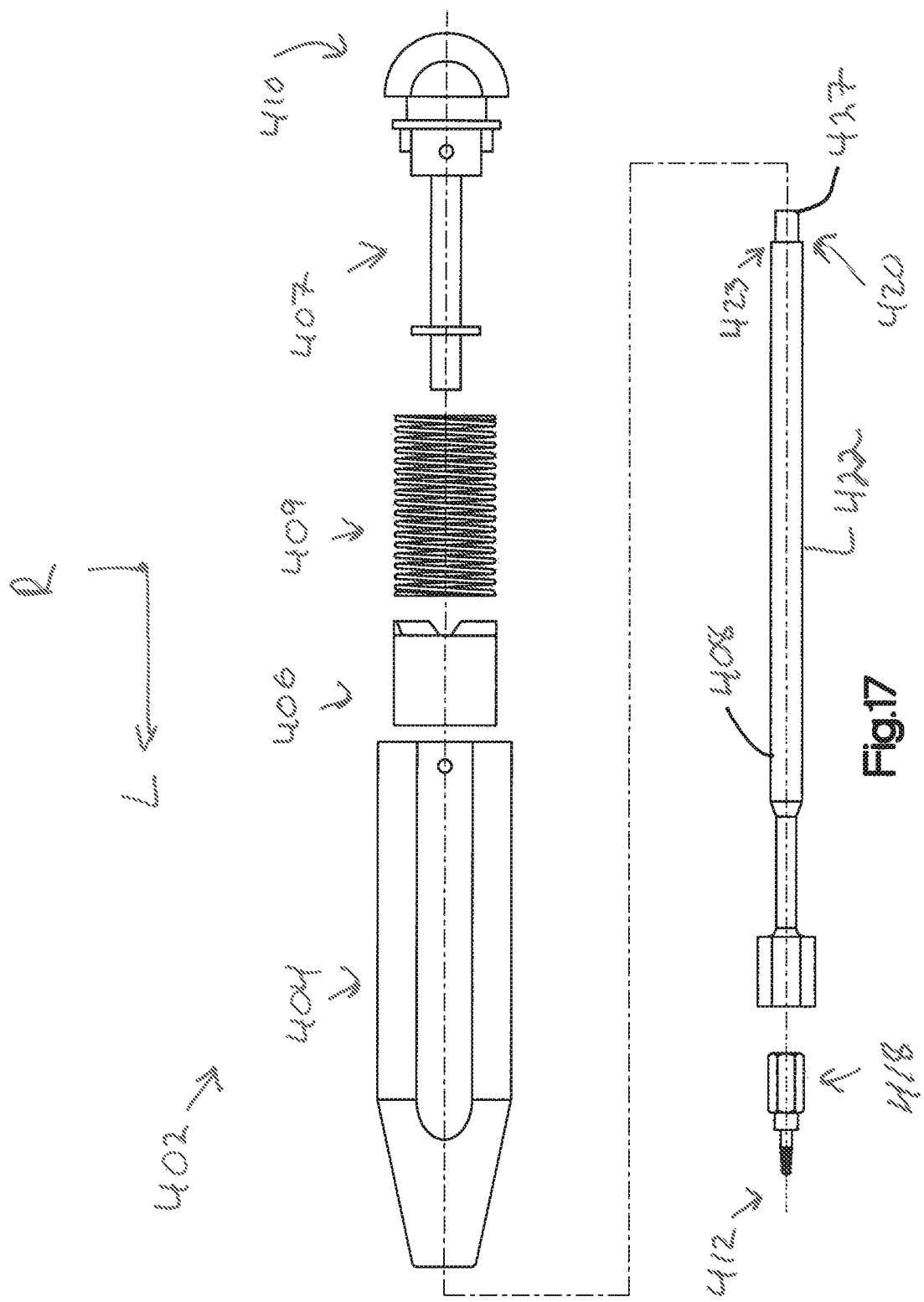
FIG. 17 is an exploded view of the instrument shown in FIG. 16.
Figure 19B:
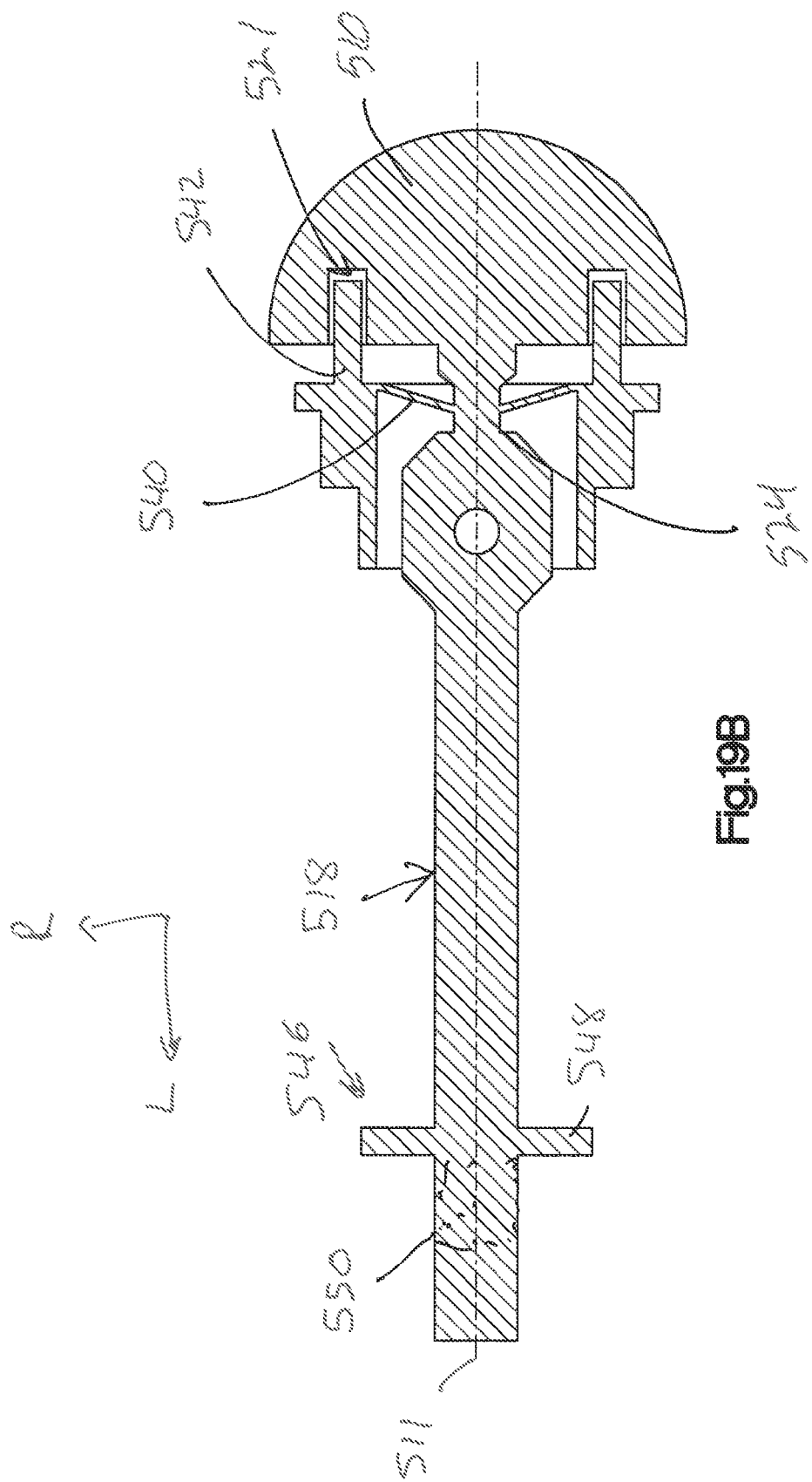

As shown in FIGS. 16 and 17, the shaft 408 can define a distal end 418, a proximal end 420 spaced apart from the distal end 418 along the longitudinal direction L, and an intermediate portion 422 disposed between the shaft proximal end 420 and distal end 418. In accordance with the alternative embodiment, the shaft distal end 418 forms the fastener engaging end 412 of the instrument 402, the intermediate portion 422 is supported by the handle 404, and the shaft proximal end 420 is rotationally fixed to the torque transfer member 406. The shaft distal end 418 can be configured as a socket 419 configured to receive a driving tip 421. The driving tip 421 can have a hex shape. The shaft distal end 418 can engage a fastener 14. The shaft proximal end 420 can be configured to engage the torque transfer member 406 such that the torque transfer member is rotationally fixed to the shaft 408 and positionally fixed along the shaft 408. That is, the torque transfer member 406 is preferably not slidable along the shaft 408 along the longitudinal direction L. The shaft proximal end 420 can define engagement member 423 configured to mate with a corresponding structure in the torque transfer member 406. The engagement member 423 can have a cross-sectional shape in the form of a cross-shape. Other shapes are possible, such as square, rectangular, star, etc., as needed. The engagement member 423 can define a tip 427. The intermediate portion 422 of the shaft can have a first cross-sectional dimension C3, and the tip 427 has a second cross-sectional dimension C4 that is less than the first cross-sectional dimension C3. The intermediate portion 422 of the shaft can have a circular cross-sectional shape that is configured to mate with the handle 404.

The handle 404 is configured to support or carry at least a portion of the actuator 407 and the torque transfer member 406. As can be seen in FIGS. 16-18, the handle 404 can define a handle body 430 that extends between a handle proximal end 432 and a handle distal end 434 spaced apart from the proximal end 432 along the longitudinal direction L. The handle body 430 can further define a handle central axis 431 that intersects a radial center (not shown) of the handle body 430. The handle axis 431 can be coaxial with the instrument axis 411. The handle body 430 defines an outer surface 436, an inner surface 438 spaced apart from the outer surface 436 along the radial direction R, and a proximally facing transverse surface 440 extending from the inner surface 438 toward the handle central axis 431 along the radial direction R. The handle body 430 includes a wall 461 extending between the outer and inner surfaces 436 and 438. The handle body inner surface 438 and the proximally facing surface 440 can define the cavity 442. Accordingly, in the illustrated embodiment, the cavity 442 extends through the handle body 430 along the longitudinal direction L from the proximal-facing surface 440 toward the handle proximal end 432. The handle body 430 also defines a proximal opening 444 in communication with the cavity 442. The opening 444 is sized to receive at least a portion of the actuator 407. The handle body 430 can include detent pairs 448 and 450 that extend from the inner surface 438 along the radial direction R at least partially into the handle body 430 toward the handle outer surface 436. The detent pairs 448 and 450 are configured to receive a portion of the actuator 407 therein. Further, the body 430 includes a transverse opening 433 that extends through the wall 461.

The handle body 430 is also configured to support a portion of the shaft 408 such that the handle 404 is rotatable relative to the shaft 408. In the illustrated embodiment, the handle body 430 can define a bore 445 that extends through the body 430 along the longitudinal direction L between the handle distal end 434 and proximal-facing surface 440. The proximal-facing surface 440 can also define an opening 447 in communication with the bore 445. The opening 447 provides a passage for the shaft. The bore 445 and opening 447 can be coaxial with the instrument axis 411. The bore 445 can have a generally cylindrical cross-sectional dimension that is complementary to the intermediate portion 422 of the shaft 408. Accordingly, the bore 445 can receive and carry the intermediate portion 422 of the shaft 408 such that the handle body 430 can rotate about the shaft 408.

The actuator 407 and torque transfer member 406 are selectively coupled so as to iterate the instrument between the active an inactive configurations. Referring to FIGS. 16-18, handle 404 carries the torque transfer member 406 in a distal most portion of cavity 442, at least a portion of the actuator 407, and a bias member 409, for instance a spring, disposed between the torque transfer member 406 and a portion of actuator 407. The bias member 409 applies a spring force to the torque transfer member 406 to bias the torque transfer member 406 in contact with the proximally surface 440 of the handle body 430.

Referring to FIG. 14, the actuator 407 extends between a proximal end 512 and an opposed distal end 514 along an actuator axis 511. The actuator proximal end 512 can also be referred to as the instrument proximal end 410. The actuator distal end 514 can engage the torque transfer member 406 (FIGS. 20A-20B). The actuator 407 can define a base 510, a moveable coupling member 516 connected to the base 510, and an elongate member 518 connected the coupling member 516. The elongate member 518 extends relative to the base 510 along the longitudinal direction L toward the actuator distal end 514. Disposed at the actuator distal end 314 is torque actuation member 546. The coupling member 516 can iterate between a first position (FIG. 19) and a second position (not shown) to selectively rotatably couple a torque actuation member 546 to the torque transfer member 406 (FIG. 16). The base 510 can define a distally facing surface 520, and a circumferential slot 521 extending from the surface 520 toward the actuator proximal end 512 along the longitudinal direction L.

The actuator 407 includes a strut 524 and a flexible member 540 connecting the strut 524 to the coupling member 518. The strut 524 also connects the base 510 to the elongate member 518. The actuator 407 is configured such that the base 510 and elongate member 518 are statically connected, while the coupling member 516 is moveably connected to the strut 524 by the flexible member 540. When the coupling member 516 is coupled to the handle 404 as further detailed below, the base 510 and the elongate member 518 can move between a first position and a second position along the longitudinal direction L. For instance, an application of a load to the proximal end 512 of the actuator 407 can cause the base 510 and elongate member 518 to translate relative to the coupling member 516 (and the handle 404).

The coupling member 516 can define a wall 526 that extends between an outer surface 528 and an inner surface 530 spaced apart from the outer surface 528 along the radial direction R. The coupling member 516 can define a pair of slats 532 and 534 that protrude from the wall 526 along the radial direction R. The slat pairs 532 and 534 are received by detent pairs 448 and 450 of the handle body 430 such that the actuator 407 is prevented from rotational movement within the handle body 430. Further, the coupling member 516 defines a ledge 536 extending from the wall 526 and forming a distal face 538 spaced apart from a proximal face 539 (FIG. 16). The distal face 538 can abut the proximal-most portion of the handle body 430 when the instrument 502 is assembled. The flexible member 540 extends between the wall 526 and the strut 524. A circumferential ridge 542 extends from the ledge 536 along the longitudinal direction L into selective engagement with the slot 521(on the base). When the ridge 542 is inserted into the slot 521, the ledge proximal face 539 abuts the surface 520 of the base 510. The distal-most portion 463 of the wall 526 defines a free end 527 that engages the bias member 409. The body 519 can include a transverse opening 533 that extends though the member body 519 along a radial direction R. When in the inactive configuration (FIG. 16), the transverse opening 533 is aligned with the handle body opening 433.

The elongate member 518 can define a body 519 that extends along the longitudinal direction L toward an actuator distal end 514. The elongate member 518 can include the torque actuation member 546 disposed at the distal end 514. The torque actuation member 546 defines a body 548, for instance a circular plate, one or more ridges 550, and a protrusion 552 which extend from the body 548 along the longitudinal direction L. The ridges 550 can be configured, for instance as a pair of ridges 550a-b. The ridge pairs 550a-550b and protrusions 552 are configured to selectively rotatably couple with the torque transfer member 406. Each ridge 550 can include an inclined surface 556, a distal face 558 spaced apart from the body 548, and a side surface 560 extending perpendicularly between the body 548 and the distal face 558. The side surface 560 can be slightly inclined relative to the body 548. The inclined surface 556 is disposed at an angle θ relative to a line perpendicular to the body 548. In an embodiment, angle θ can vary between about 20 degrees and about 75 degrees. In the illustrated embodiment, the angle θ (not shown) is about 45 degrees. It will be appreciated that the inclined surface can be linear, as shown, or curvilinear as needed. The ridge pairs 550a and 550b are disposed such that the inclined surfaces 556 of each are facing the rotation direction 3.

The torque transfer member 406 defines a body 462 and a one or more ridges 464 protruding from the body 462. The one or more ridges can be a pair of ridges 464a, 464b. The ridge pairs 464a, 464b protrude from the torque transfer member body 462 to couple with the corresponding ridge pairs 550a and 550b. The ridge pairs 464a and 464b of the torque transfer member 406 are configured similarly to the ridge pairs 550a and 550b of the actuator 407. However, the inclined surfaces 466 of the ridge pairs 464 face a second rotation direction 5 (that is opposite the first rotation direction 3) so as to abut the inclined surfaces 556 of the actuator 407. The torque transfer member body 462 extends between a proximal end 468 and a distal end 470 spaced apart from the proximal end 468 along instrument axis 411. The body 462 can define a bore 446 that extends between the proximal end 468 and the distal end 470. The bore 446 can define a ridge 473 that extends from the body 462 into a portion of the bore 446 to divide the bore 446 into two portions. Accordingly, the bore 446 can have a shaft engaging or first portion 474 extending distally from the ridge 473, and an actuator engaging or second portion 476 extending proximally from the ridge 473. The shaft engaging portion 474 can have a cross-sectional shape that corresponds to the cross-sectional shape of the engagement member 423 of the shaft 408, and for instance can have a cross-shape. When the shaft engagement member 423 is inserted into the shaft engaging portion 474, the torque transfer member 406 is rotationally fixed relative to the shaft 408 and the tip 427 abuts the ridge 473. The actuator engaging portion 476 can have a cross-sectional shape that corresponds to the cross-sectional shape of the actuator protrusion 552. For instance, the actuator engaging portion 476 can be cylindrical such that the protrusion can selectively slide and/or rotate therein.

When the instrument 402 is operated to drive a fastener 14 into the fastening location 16, the actuator 407 can be actuated into the active configuration. To actuate the instrument 402, the actuator base 510 is moved along the longitudinal direction L to flex or deform the flexible member 540 such that the base 510 and elongate member 518 translate relative to the coupling member 516 and handle 404. During actuation, the base slot 521 receives the coupling member ridge 542, while the protrusion 552 is displaced into the bore 446 of the torque transfer member 406. The actuator wall 526 (wall free end 527) further compresses the bias member 409 such that the actuator ridges 550 abut the ridges 472 of torque transfer member so that the torque actuation member 546 is rotatably coupled to the torque transfer member 406. When the instrument 402 is in the active configuration and a torque is applied to the handle 404 along the rotation direction 3, the handle 404 transmits the applied torque TA through the torque transfer member 406 to the shaft 408 so that the handle 404, torque transfer member 406 and shaft 408 rotate together. As the torque applied to the handle increases, the torque transfer member 406 rotates relative to the torque actuation member 546 so that ridge 472, 550 slide with respect to each other. Further rotation displaces the torque transfer member 406 against the spring force of the bias member 409. When the applied torque TA is greater than the limited torque value TV, the torque transfer member 406 displaces the torque actuation member 546 deflecting the flexible member 540 and further compresses the spring so that the ridges 472 and 550 slip past each other. As the ridges 472 and 550 slip, the handle 4 rotates with respect to the torque transfer member 406 and the shaft 408.

Another embodiment of the present disclosure includes a method of producing a torque limiting driving instrument in accordance with the embodiments described above and illustrated in FIGS. 16-20B. The method includes the steps of forming the handle 404 and the torque transfer member 406. Further, the method can include the step of forming the actuator 407. The handle 404, torque transfer member 406 and/or actuator 407 can be formed of a polymeric material. In accordance with an alternative embodiment, the method can include the step of compounding the polymer or polymers, additives, lubricants and other processing agents to form a polymeric compound. The polymeric compound can be formed into the handle 404, torque transfer member 406 and/or actuator 407 using such plastic forming or compounding methods that can be used such as injection molding, blow molding and/or reactive injection molding. The compounding and forming steps can occur separately, sequentially, or together in a single step. A curing step can be included for thermosets. Further, when metallic material is used to form one of the handle or torque limiting member, CNC machining or other metal forming processes can be used. The handle 404 or torque transfer member 406 and actuator 407 forming steps can include forming the respective handle 404, torque transfer member 406, and actuator 407 to have the structural details described above and shown in FIGS. 16-20B.

Further, the method of producing the instruments illustrated in FIGS. 16-20B can include assembling the handle 404, torque transfer member 406, shaft 408, and actuator 407 to form an instrument 402 with a specified torque limit. The method can include attaching the shaft 408 to the torque transfer member 406 such that the shaft 408 extends from the torque transfer member 406 along the instrument axis 11. The method can also include attaching the torque transfer member 406 to the handle 404 by inserting the torque transfer member 406 (with or without the shaft) into the handle cavity 442. Further, the method can include placing a bias member 409 in the handle 404 into engagement with the torque transfer member 406. The actuator 407 can be coupled to the handle 404 and the torque transfer member 406. During placement of the actuator, the actuator can bias the bias member so that biasing force is applied to a portion of the torque transfer member 406 and the actuator 407. Further, the method can include packaging the instrument 402 into a sterile container, for instance, individually packaging the instrument in a sterile container.

An embodiment of the present disclosure also includes a surgical kit including two or more torque limiting instruments, for example a first driving instrument and a second driving instrument. The first and second instruments can be configured according to any of the embodiments as described and shown in FIGS. 1-20B. However, the first driving instrument is configured to rotate the first fastener along a first rotation direction 3 until a first torque limit is attained. The first torque limit can be, for example, 0.8 nM. The second driving instrument is 610 configured to rotate the second fastener along the first rotation direction 3 until a second torque limit is attained. The second torque limit can be, for example, 4.0 nM. The torque limits for the instruments can range any specific limit. In an embodiment, either the first torque limiting instrument, the second torque limiting instrument, or both the first and second torque limiting instruments, are limit torque transferred to the shaft when the torque is applied along a first rotation direction, is configured such that rotation along a second rotation direction 5 that is opposite the first rotation direction 3 allows rotation of the fastener along the second rotation direction 5 regardless of the torque applied in the second rotation direction 5. That is, the instruments are configured to limit torque in one rotation direction, wherein the rotation direction is same direction as the rotation direction for tightening the fastener in position, while not including a torque limit when the fastener is rotated in a loosening rotation direction.

It should be appreciated that any single component or combination of two or more components as described herein may form an exemplary embodiment of the invention. For example, any the combination of the handle and torque limiting member, or portions of the handle and torque limiting member, as well as various steps of the methods and described herein may form varying embodiments of the invention. Further, certain features of each of these aforementioned components in one embodiment may be used with the other features of different components as needed in other embodiments as well. For example, any one or combination of materials as disclosed herein may be used in various components or combinations of components on the various embodiments of the instrument device.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate that instruments, devices, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A method for limiting torque that is transferred from a handle end of a driving instrument through a torque transfer member to a shaft that extends from the handle along an instrument axis, at least a portion of the torque transfer member received in a cavity of the handle, the cavity extending inwardly in a radial direction from a wall of the handle toward the instrument axis, the radial direction being perpendicular to the instrument axis, the method comprising the steps of:

applying a torque to the handle along a direction relative to the shaft;

transmitting the applied torque from the handle through the torque transfer member to the shaft when the applied torque is less than a limited torque value; and deforming at least a portion of the wall in the radial direction with the torque transfer member when the applied torque is greater than the limited torque value so as to allow the handle to rotate along the rotation direction relative to both the torque transfer member and the shaft when the applied torque is greater than the limited torque value.

2. The method of claim 1, wherein the steps of transmitting and deforming occurs while maintaining the handle and the torque transfer member stationary on the instrument axis between an instrument proximal end and an opposing instrument distal end.

3. The method of claim 1, wherein the torque transfer member comprises a base and a protrusion that extends from the base, the protrusion coupled to a complementary structure of the handle.

4. The method of claim 3, wherein the step of deforming further comprises: deforming the handle from a first configuration into a second configuration, whereby the first configuration is defined as when the handle is not permitted to rotate relative to the torque transfer member and the shaft, and the second configuration is defined as when the applied torque is greater than the limited torque value and the handle is deformed so as to allow the handle to rotate along the direction relative to both the torque transfer member and the shaft.

5. The method of claim 1, wherein the handle comprises a body and a protrusion that extends from the body, the protrusion of the body coupled to a complementary structure of the torque transfer member.

6. The method of claim 1, wherein the driving instrument defines a proximal end and an engaging end spaced apart from the proximal end along the instrument axis, the handle or the torque transfer member define at least one groove that extends at least partially along the instrument axis, and the other of the handle and the torque transfer member defines a body and at least one protrusion that extends from the body, and wherein the at least one protrusion is coupled with the at least one groove, wherein the step of deforming further comprises: decoupling the at least one protrusion from the at least one groove.

7. The method of claim 6, wherein the at least one protrusion is at least one flexible tab that extends from the base to engaging a corresponding at least one groove, wherein the step of deforming further comprises: deforming the at least one flexible tab out of engagement with the at least one groove.

8. A method of producing a torque limiting driving instrument, the driving instrument configured to drive a fastener into a fastening location, the driving instrument defining a proximal end and a fastener engaging end spaced apart from the proximal end along an instrument axis, the method comprising:
  attaching a shaft to a torque transfer member such that the shaft extends from the torque transfer member along a central axis; and
  attaching the torque transfer member to a handle, such that at least one of the torque transfer member or the handle defines at least one protrusion that is configured to abut the other of the torque transfer member or the handle,
  wherein a peripheral wall of the handle is configured to deform in a radial direction that is perpendicular to the central axis in response to a torque applied to the handle greater than a limited torque value, thereby allowing the handle to rotate with respect to the shaft, wherein the peripheral wall extends from an outer surface of the handle to an inner surface of the handle in the radial direction.

9. The method of claim 8, wherein the handle defines an inner cavity configured to receive the torque limiting member, and the step of attaching the torque transfer member to the handle further comprises: inserting the torque transfer member into the inner cavity.

10. The method of claim 8, wherein the torque transfer member defines a cavity configured to receive the handle member, and the step of attaching the torque transfer member to the handle further comprises: inserting the handle into the torque transfer member cavity.

11. The method of claim 8, wherein the torque transfer member defines a base and at least one flexible tab that extends from the base, and the handle defines at least one groove, wherein the step of attaching the torque transfer member to the handle further comprises: positioning the torque transfer member such that the at least one flexible tab is received at least partially by the at least one groove of the handle.

12. A torque limiting driving instrument for driving an anchor into a surgical site, the driving instrument defining a proximal end, and a distal end spaced apart from the proximal end along an instrument axis, the driving instrument comprising:

a handle having a wall and defining a cavity extending inwardly from the wall toward the instrument axis in a radial direction that is perpendicular to the instrument axis;
  a torque transfer member coupled to the handle at least partially within the cavity, the torque transfer member having at least one protrusion that extends from the torque transfer member, wherein the torque transfer member is coupled to the handle such that the at least one protrusion abuts a complementary structure of the handle; and
  a shaft that extends from the torque transfer member along the instrument axis to an anchor engaging end, wherein the shaft is rotationally fixed to the torque transfer member,
  wherein the wall of the handle is deformable in the radial direction such that the handle is selectively rotatable relative to the torque transfer member, and wherein the driving instrument is configured to rotate the anchor along a rotation direction until a torque applied to the handle is greater than a limited torque value.

13. The driving instrument of claim 12 wherein the handle and the torque transfer member are stationary relative to the proximal and distal ends of the driving instrument when a torque applied to the handle is less than the limited torque value.

14. The driving instrument of claim 12, wherein the complementary structure of the handle is at least one groove formed in the wall, the at least one groove extending at least partially along the instrument axis.

15. The driving instrument of claim 12, wherein at least one of the handle and the torque transfer member is polymeric.

16. The driving instrument of claim 12, wherein the driving instrument is configured to iterate between a first configuration and a second configuration, wherein the first configuration is defined as when the handle is not rotatable relative to the torque transfer member and the shaft, and wherein the second configuration is defined as when the applied torque is greater than the limited torque value so that the handle is rotatable relative the torque transfer member and the shaft.

17. The driving instrument of claim 12, wherein the wall is configured to radially deform so as to allow the handle to rotate relative to the torque transfer member and the shaft.

18. The driving instrument of claim 12, wherein the complementary structure of the handle is at least one groove formed in the wall.

19. The driving instrument of claim 12, wherein the at least one protrusion is at least one tab that extends from the torque transfer member to engage a corresponding at least one groove of the handle.

* * * * *